(12) United States Patent
Shimomura

(10) Patent No.: US 11,419,480 B2
(45) Date of Patent: Aug. 23, 2022

(54) NAVIGATION DEVICE, NAVIGATION METHOD, AND ENDOSCOPE SYSTEM

(71) Applicant: FUJIFILM Corporation, Tokyo (JP)

(72) Inventor: Koji Shimomura, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 948 days.

(21) Appl. No.: 16/194,402

(22) Filed: Nov. 19, 2018

(65) Prior Publication Data

US 2019/0082930 A1 Mar. 21, 2019

Related U.S. Application Data

(63) Continuation of application No. PCT/JP2017/018211, filed on May 15, 2017.

(30) Foreign Application Priority Data

Jun. 16, 2016 (JP) .............................. JP2016-119782

(51) Int. Cl.
*A61B 1/00* (2006.01)
*A61B 34/20* (2016.01)
(Continued)

(52) U.S. Cl.
CPC ...... *A61B 1/00006* (2013.01); *A61B 1/00009* (2013.01); *A61B 1/05* (2013.01);
(Continued)

(58) Field of Classification Search
CPC . A61B 1/00006; A61B 1/00158; A61B 1/005; A61B 1/0009; A61B 34/20;
(Continued)

(56) References Cited

U.S. PATENT DOCUMENTS 6,295,368 B1 9/2001 Hasegawa et al.
2005/0228221 A1* 10/2005 Hirakawa .......... A61B 1/00009
600/101

(Continued)

FOREIGN PATENT DOCUMENTS

CN 101455554 6/2009
CN 101820810 9/2010
(Continued)

OTHER PUBLICATIONS

"International Search Report (Form PCT/ISA/210) of PCT/JP2017/018211," dated Jul. 25, 2017, with English translation thereof, pp. 1-5.

(Continued)

*Primary Examiner* — Ryan N Henderson
*Assistant Examiner* — Pamela F Wu
(74) *Attorney, Agent, or Firm* — JCIPRNET

(57) ABSTRACT

Provided are a navigation device and a navigation method capable of reducing the size and the cost of an endoscope, and an endoscope system including the navigation device. The navigation device includes a magnetic field generation control unit that causes magnetic fields to be generated at different timings from a plurality of magnetic field generation units that generate the magnetic fields at mutually different positions; an image signal acquisition unit that acquires, from the endoscope, an added image signal obtained by adding specification information for specifying the magnetic field generation units generating the magnetic fields and magnetic field detection results of the respective magnetic field detection units to an image signal output from an imaging element; and a position detection unit that detects positions of the respective magnetic field detection units on the basis of the specification information and the (Continued)

magnetic field detection results that are added to the added image signal acquired by the image signal acquisition unit.

23 Claims, 15 Drawing Sheets

(51) Int. Cl.
  *A61B 5/06* (2006.01)
  *A61B 1/05* (2006.01)
  *G01R 33/28* (2006.01)
  *G01R 33/54* (2006.01)
(52) U.S. Cl.
  CPC .............. *A61B 5/065* (2013.01); *A61B 34/20* (2016.02); *G01R 33/285* (2013.01); *G01R 33/543* (2013.01); *A61B 2034/2051* (2016.02)
(58) Field of Classification Search
  CPC ........ A61B 2034/2051; A61B 1/00016; A61B 1/00009; G02R 33/285; G01R 33/543
  USPC .................................. 600/114, 117, 118, 139
  See application file for complete search history.

(56) References Cited

U.S. PATENT DOCUMENTS

| | | | |
|---|---|---|---|
| 2007/0106114 A1* | 5/2007 | Sugimoto | .............. A61B 5/068 600/117 |
| 2007/0106115 A1 | 5/2007 | Sugimoto | |
| 2008/0097155 A1 | 4/2008 | Gattani et al. | |
| 2009/0030306 A1 | 1/2009 | Miyoshi et al. | |
| 2009/0149711 A1 | 6/2009 | Tanaka et al. | |
| 2010/0204566 A1 | 8/2010 | Uchiyama et al. | |
| 2015/0297062 A1* | 10/2015 | Golenberg | ............. A61B 90/37 348/68 |

FOREIGN PATENT DOCUMENTS

| | | |
|---|---|---|
| JP | H11295618 | 10/1999 |
| JP | 2000157486 | 6/2000 |
| JP | 2002165756 | 6/2002 |
| JP | 2004147778 | 5/2004 |
| JP | 2006212187 | 8/2006 |
| JP | 2007130144 | 5/2007 |
| JP | 2007130174 | 5/2007 |
| JP | 2007130175 | 5/2007 |
| JP | 2008119260 | 5/2008 |
| JP | 2009039356 | 2/2009 |
| JP | 2011024606 | 2/2011 |
| WO | 2014208630 | 12/2014 |

OTHER PUBLICATIONS

"Written Opinion of the International Searching Authority (Form PCT/ISA/237) of PCT/JP2017/018211," dated Jul. 25, 2017, with English translation thereof, pp. 1-12.

"Search Report of Europe Counterpart Application", dated May 23, 2019, p. 1-p. 9.

"Office Action of China Counterpart Application", dated Jul. 1, 2020, with English translation thereof, pp. 1-11.

* cited by examiner

NAVIGATION DEVICE, NAVIGATION METHOD, AND ENDOSCOPE SYSTEM

CROSS-REFERENCE TO RELATED APPLICATIONS

The present application is a Continuation of PCT International Application No. PCT/JP2017/018211 filed on May 15, 2017 claiming priority under 35 U.S.C § 119(a) to Japanese Patent Application No. 2016-119782 filed on Jun. 16, 2016. Each of the above applications is hereby expressly incorporated by reference, in their entirety, into the present application.

BACKGROUND OF THE INVENTION

1. Field of the Invention

The present invention relates to a navigation device and a navigation method of an endoscope, and an endoscope system including the navigation device.

2. Description of the Related Art

In the related art, endoscopic examination using an electronic endoscope (hereinafter simply referred to as an endoscope) has been performed in the medical field (refer to JP2000-157486A, JP2004-147778A, JP2008-119260A, and JP1999-295618 (H11-295618A)). For example, an endoscope used for examination of an upper alimentary canal, a lower alimentary canal, and the like has a flexible (soft) insertion part to be inserted into a patient's alimentary canal. An imaging device constituted of an imaging optical system, an imaging element, and the like is provided within a distal end part of the insertion part. By imaging a region to be observed within the alimentary canal with the imaging device, an observation image of the region to be observed is obtained.

In such endoscopic examination, it is preferable to simultaneously acquire the shape of the insertion part within the alimentary canal in addition to the observation image of the region to be observed within the alimentary canal. Accordingly, an operator can perform the insertion operation of the insertion part more smoothly and safely.

For example, JP2007-130175A, JP2006-212187A, and JP2007-130144A disclose endoscope systems including a magnetic field generator having a plurality of coils that generate magnetic fields through application of an alternating current; an endoscope in which a plurality of coils for detecting the magnetic fields generated from the magnetic field generator are provided within the insertion part; and a detecting device (equivalent to a navigation device including a processor) connected to the endoscope. In the endoscope systems of the respective JP2007-130175A, JP2006-212187A, and JP2007-130144A, magnetic field detection results (induced current values) obtained by the respective coils within the insertion part are output from the endoscope to the detecting device, and the shape of the insertion part within an alimentary canal is detected by detecting the positions of the respective coils with the detecting device on the basis of the magnetic field detection results of the respective coils.

SUMMARY OF THE INVENTION

Meanwhile, in the endoscope systems described in the above JP2007-130175A, JP2006-212187A, and JP2007-130144A, it is necessary to separately provide the endoscope with an output system for outputting the magnetic field detection results detected by the respective coils within the insertion part to the detecting device in addition to an output system for outputting the image signals imaged by the imaging device of the distal end part to the processor. For this reason, in a case where the shape of the insertion part of the endoscope is detected using methods described in the above JP2007-130175A, JP2006-212187A, and JP2007-130144A, problems of increases in size and manufacturing cost of the endoscope occur.

The invention has been made in view of such circumstances, and an object thereof is to provide a navigation device and a navigation method capable of reducing the size and the cost of an endoscope, and an endoscope system including the navigation device.

A navigation device for achieving the object of the invention is a navigation device used for an endoscope having an insertion part to be inserted into a subject, an imaging element provided on a distal end side of the insertion part, and a plurality of magnetic field detection units that are provided within the insertion part and detect magnetic fields. The navigation device comprises a magnetic field generation control unit that causes the magnetic fields to be generated at different timings from a plurality of magnetic field generation units that generate the magnetic fields at mutually different positions; an image signal acquisition unit that acquires, from the endoscope, an added image signal obtained by adding specification information for specifying the magnetic field generation units generating the magnetic fields and magnetic field detection results of the respective magnetic field detection units to an image signal output from the imaging element; and a position detection unit that detects positions of the respective magnetic field detection units on the basis of the specification information and the magnetic field detection results that are added to the added image signal acquired by the image signal acquisition unit.

According to this navigation device, since the added image signal to which the magnetic field detection results are added can be output from the endoscope to the navigation device, it is unnecessary to separately provide the endoscope with an output system for outputting the magnetic field detection results to the navigation device.

In the navigation device according to another aspect of the invention, the image signal is a plurality of frame image signals that constitute a dynamic image, and the added image signal is added frame image signals obtained by adding the specification information and the magnetic field detection results to the frame image signals. The specification information is frame start signals showing start of the added frame image signals. The magnetic field generation control unit performs switching of the magnetic field generation units generating the magnetic fields on the basis of the frame start signals added to the added frame image signals acquired by the image signal acquisition unit. The position detection unit performs determination processing of determining a correspondence relationship between the magnetic field detection results added to the added frame image signals and the magnetic field generation units, on the basis of the frame start signals added to the added frame image signals, and position detection processing of detecting the positions of the respective magnetic field detection units from the magnetic field detection results, on the basis of the correspondence relationship determined by the determination processing. Accordingly, since the correspondence relationship between the magnetic field detection results and the magnetic field generation units can be determined on the basis of the frame start signals, the positions of the respective magnetic field detection units can be detected from the magnetic field detection results acquired from the endoscope.

In the navigation device according to still another aspect of the invention, the magnetic field generation control unit causes the magnetic fields to be generated in different generation patterns for the respective magnetic field generation units. The specification information is included as the generation patterns in the magnetic field detection results. The position detection unit performs determination processing of determining the magnetic field generation units corresponding to the magnetic field detection results on the basis of the generation patterns detected from the magnetic field detection results added to the added image signal, and position detection processing of detecting the positions of the respective magnetic field detection units from the magnetic field detection results, on the basis of the determination results of the determination processing. Accordingly, since the correspondence relationship between the magnetic field detection results and the magnetic field generation units can be determined on the basis of the generation patterns, the positions of the respective magnetic field detection units can be detected from the magnetic field detection results acquired from the endoscope.

In the navigation device according to a still further aspect of the invention, the image signal is a plurality of frame image signals that constitute a dynamic image, and the added image signal is added frame image signals obtained by adding the specification information and the magnetic field detection results to the frame image signals. The magnetic field detection results are added to a signal invalid region between the added frame image signals corresponding to a blank time of the imaging element. Accordingly, the magnetic field detection results can be added to the frame image signals and can be output to the navigation device.

In the navigation device according to a still further aspect of the invention, the image signal acquisition unit acquires the added image signal from the endoscope by performing noncontact communication with the endoscope. Accordingly, the added image signal can be acquired from the endoscope.

The navigation device according to a still further aspect of the invention further comprises an insertion part shape detection unit that detects a shape of the insertion part within the subject on the basis of a position detection result obtained by the position detection unit. Accordingly, an operator can ascertain the shape of the insertion part within the subject.

An endoscope system for achieving the object of the invention comprises an endoscope having an insertion part to be inserted into a subject, an imaging element provided on a distal end side of the insertion part, and a plurality of magnetic field detection units that are provided within the insertion part and detect magnetic fields; a plurality of magnetic field generation units that generate the magnetic fields; and the aforementioned navigation device.

In the endoscope system according to a still further aspect of the invention, the endoscope is provided with an image signal output unit that adds the specification information for specifying the magnetic field generation units generating the magnetic fields and the magnetic field detection results for the respective magnetic field detection units, to the image signal output from the imaging element, and outputs the added image signal, to which the specification information and the magnetic field detection results are added, to the navigation device. Accordingly, it is unnecessary to separately provide the endoscope with the output system for outputting the magnetic field detection results to the navigation device.

In the endoscope system related to still another aspect of the invention, the magnetic field generation units are provided at positions different from the endoscope.

A navigation method for achieving the object of the invention is a navigation method used for an endoscope having an insertion part to be inserted into a subject, an imaging element provided on a distal end side of the insertion part, and a plurality of magnetic field detection units that are provided within the insertion part and detect magnetic fields. The navigation method comprises a magnetic field generation control step of causing the magnetic fields to be generated at different timings from a plurality of magnetic field generation units that generate the magnetic fields at mutually different positions; an image signal acquisition step of acquiring, from the endoscope, an added image signal obtained by adding specification information for specifying the magnetic field generation units generating the magnetic fields and magnetic field detection results of the respective magnetic field detection units to an image signal output from the imaging element; and a position detection step of detecting positions of the respective magnetic field detection units on the basis of the specification information and the magnetic field detection results that are added to the added image signal acquired in the image signal acquisition step.

In the navigation device, the navigation method, and the endoscope system of the invention, the size and the cost of the endoscope can be reduced.

DESCRIPTION OF THE PREFERRED EMBODIMENTS

Overall Configuration of Endoscope System of First Embodiment

Figure 1:
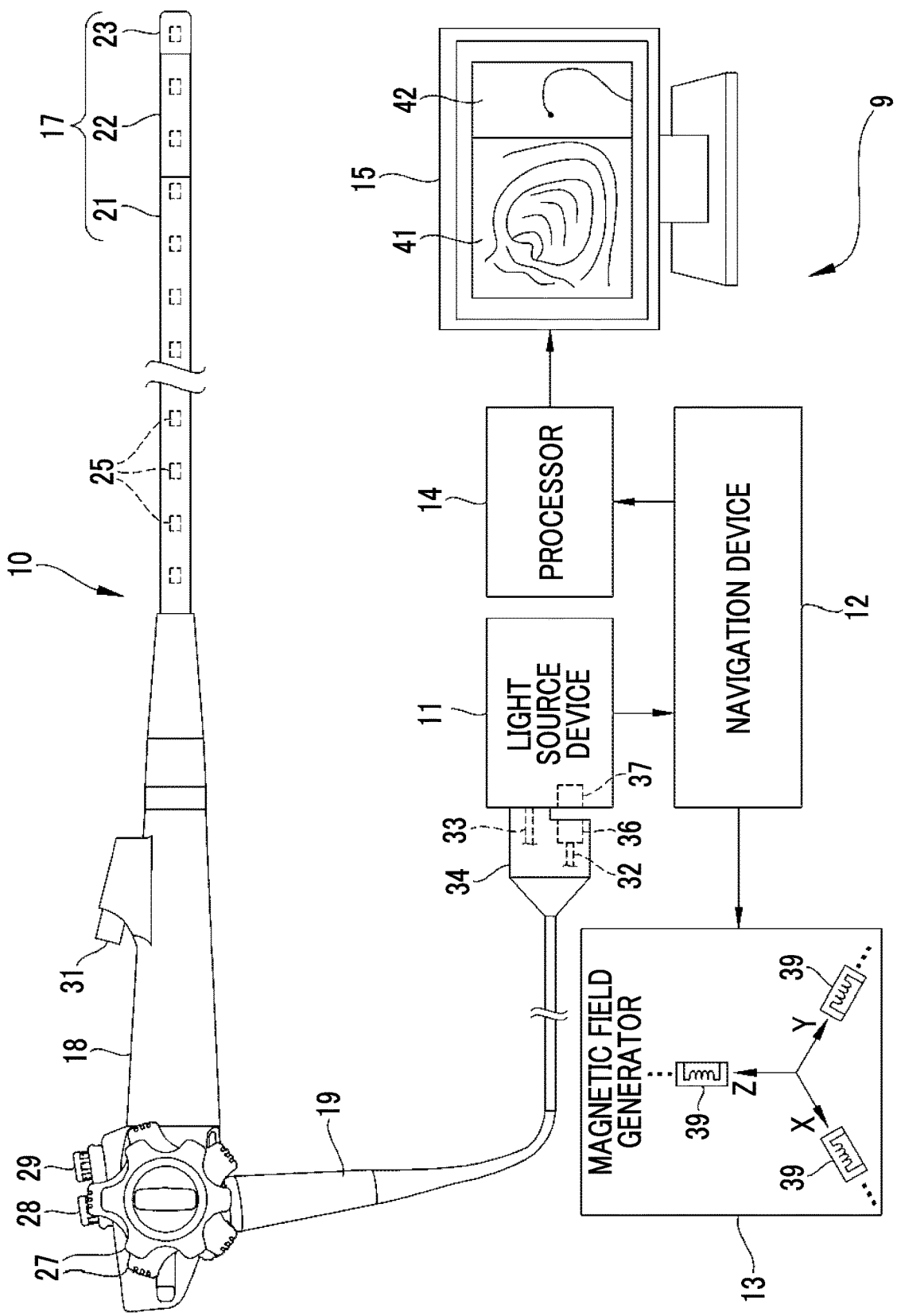
FIG. 1 is a schematic view illustrating an overall configuration of an endoscope system of a first embodiment.

FIG. 1 is a schematic view illustrating an overall configuration of an endoscope system 9 of the first embodiment. As illustrated in FIG. 1, the endoscope system 9 includes an endoscope 10, a light source device 11, a navigation device 12, a magnetic field generator 13, a processor 14, and a monitor 15.

The endoscope 10 is, for example, a flexible endoscope used for examining the inside of a subject (alimentary canal). The endoscope 10 has an insertion part 17 that is inserted into the alimentary canal and has a distal end and a proximal end, an operating part 18 that is provided continuously with a proximal end side of the insertion part 17 and performs various operations by being gripped by an operator, and a universal cord 19 provided continuously with the operating part 18.

The entire insertion part 17 is formed in an elongated shape with a fine diameter. The insertion part 17 is configured such that a flexible part 21 having flexibility, a bending part 22 that is bendable by the operation of the operating part 18, a distal end part 23 where an imaging device 48 (refer to FIG. 2) and the like are disposed are continuously provided in order toward a distal end side from the proximal end side. Additionally, a plurality of detection coils 25 are provided at predetermined intervals from the flexible part 21 to the distal end part 23 within the insertion part 17.

The respective detection coils 25 are equivalent to a magnetic field detection unit of the invention, and receives magnetic fields generated from a magnetic field generator 13 (to be described below), respectively, to generate induced currents caused by electromagnetic induction. The values of the induced currents generated from the respective detection coils 25 are magnetic field detection results (magnetic field detection data 55; refer to FIG. 2) obtained by detecting the magnetic fields generated from the magnetic field generator 13 with the respective detection coils 25, respectively.

The operating part 18 is provided with various operating members to be operated by the operator. Specifically, the operating part 18 is provided with two types of bendable operation knobs 27 used for a rightward and leftward bending operation and an upward and downward bending operation of the bending part 22, an air/water supply button 28, and a suction button 29.

Additionally, the operating part 18 is provided with a treatment tool introduction port 31 that allows a treatment tool to be inserted into a treatment tool insertion passage (not illustrated) passing through the insertion part 17.

The universal cord 19 is a connecting cord for connecting the endoscope 10 to the light source device 11. The universal cord 19 encapsulates a signal cable 32 inserted through the insertion part 17, a light guide 33, and a fluid tube (not illustrated). Additionally, an end part of the universal cord 19 is provided with a connector 34 connected to the light source device 11.

By connecting the connector 34 to the light source device 11, electrical power, control signals, illumination light, gas, and water, which are required for the operation of the endoscope 10, are supplied from the light source device 11 to the endoscope 10. Additionally, image signals of a region to be observed, which are acquired by the imaging device 48 (refer to FIG. 2) of the distal end part 23, and the magnetic field detection results (induced current values) of the respective detection coils 25 are transmitted from the endoscope 10 to the light source device 11.

The connector 34 is not electrically wire-connected to the light source device 11, and performs transmission and reception of the control signals exchanged between the endoscope 10 and the light source device 11, and transmission of the image signals and the magnetic field detection results from the endoscope 10 to the light source device 11 through optical communication (noncontact communication). The connector 34 is provided with a laser diode (hereinafter abbreviated as an LD) 36 connected to the signal cable 32.

The LD 36 is used for transmission of mass data from the endoscope 10 to the light source device 11, specifically, for transmission of the image signals and magnetic field detection results. The LD 36 transmits optical signals obtained by conversion of the image signals and the magnetic field detection results, which are electrical signals, toward a photodiode (hereinafter abbreviated as a PD) 37 provided in the light source device 11.

In addition, although illustration is omitted, both of the connector 34 and the light source device 11 are provided with optical transmission/reception units that convert small-capacity control signals exchanged between the endoscope 10 and the light source device 11 into optical signals, and transmit and receive the optical signals. Moreover, the connector 34 is provided with a power receiving unit (not illustrated) that receives power by wireless power feed from a power feeding unit (not illustrated) of the light source device 11.

The light guide 33 within the connector 34 is inserted into the light source device 11. Additionally, the fluid tube (not illustrated) within the connector 34 is connected to an air/water supply device (not illustrated) via the light source device 11. Accordingly, illumination light, gas, and water are respectively supplied from the light source device 11 and the air/water supply device to the endoscope 10.

The light source device 11 supplies the illumination light to the light guide 33 of the endoscope 10 via the connector 34 and supplies the gas and the water, which have been supplied from air/water supply device (not illustrated), to the fluid tube (not illustrated) of the endoscope 10. Additionally, the light source device 11 receives the optical signals transmitted from the LD 36 with the PD 37, converts the received optical signals into original image signals and magnetic field detection results that are electrical signals, and then outputs the converted signals to the navigation device 12.

The navigation device 12 outputs the image signals, which have been input from the light source device 11, to the processor 14. Additionally, the navigation device 12 controls driving of the magnetic field generator 13 (to be described below), and detects the shape or the like of the insertion part 17 within the subject to output this detection result to the processor 14.

The magnetic field generator 13 is provided at positions different from the endoscope 10, and has the plurality of generation coils 39 equivalent to the magnetic field generation unit of the invention. The generation coils 39 respectively include, for example, an X-axis coil, a Y-axis coil, and a Z-axis coil that generate alternating current magnetic fields in directions corresponding to the XYZ coordinate axes of the orthogonal coordinate system XYZ, by application of driving currents. Although the respective generation coils 39 will be described below in detail, the respective generation coils 39 generates magnetic fields at mutually different timings under the control of the navigation device 12.

The processor 14 outputs the image signals input from the navigation device 12, and the detection result of the shape or the like of the insertion part 17, to the monitor 15. The monitor 15 displays the observation image 41 (dynamic image) on the basis of the image signals input from the navigation device 12, and displays the insertion part shape image 42 showing the shape or the like of the insertion part 17 on the basis of the detection result of the shape or the like of the insertion part 17. In addition, monitors 15 that display the observation image 41 and the insertion part shape image 42 may be separately provided, respectively.

<Endoscope>

Figure 2:
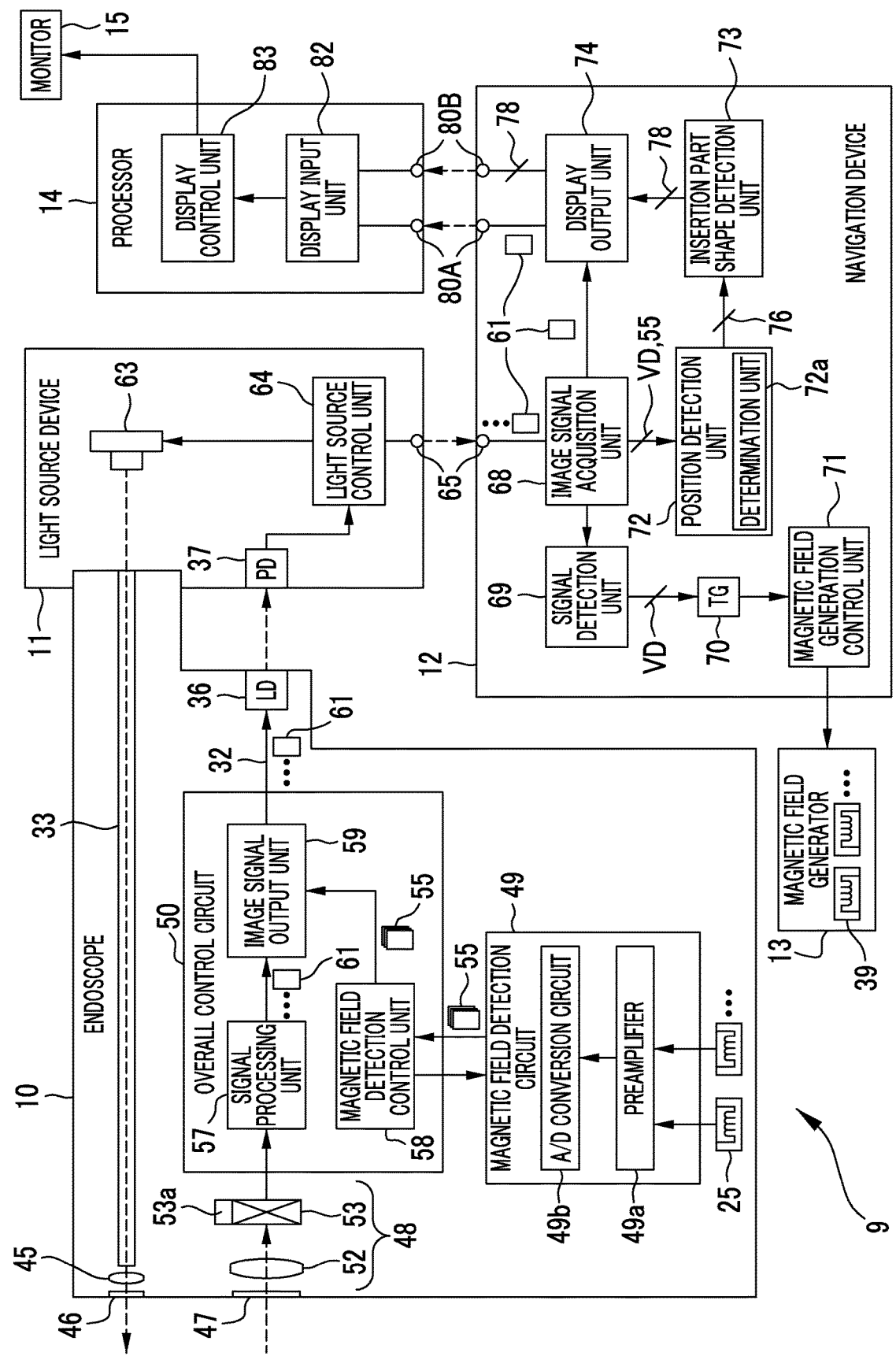
FIG. 2 is a block diagram illustrating an electric configuration of the endoscope system of the first embodiment.

FIG. 2 is a block diagram illustrating an electric configuration of the endoscope system 9 of the first embodiment. As illustrated in FIG. 2, the endoscope 10 has the light guide 33, an irradiation lens 45, an illumination window 46, an observation window 47, the imaging device 48, a magnetic field detection circuit 49, an overall control circuit 50, the signal cable 32, the LD 36, the fluid tube (not illustrated), and an air/water supply nozzle (not illustrated).

A light guide 33 is a large-diameter optical fiber, a bundle fiber, or the like. An incident end of the light guide 33 is inserted into the light source device 11 via the connector 34. An exit end of the light guide 33 passed through the connector 34, the universal cord 19, and the operating part 18, and faces the irradiation lens 45 provided within the distal end part 23 of the insertion part 17. Accordingly, the illumination light supplied from the light source device 11 to the incident end of the light guide 33 is radiated to the region to be observed through the illumination window 46 provided on a distal end surface of the distal end part 23 from the irradiation lens 45. The illumination light reflected or scattered in the region to be observed is incident on the imaging device 48 through the observation window 47 provided on the distal end surface of the distal end part 23, as image light of the region to be observed.

In addition, one end side of the aforementioned fluid tube (not illustrated) is connected to the air/water supply device (not illustrated) through the connector 34 and the light source device 11, and the other end side of the fluid tube (not illustrated) is connected to the air/water supply nozzle (not illustrated) provided on the distal end surface of the distal end part 23 through the inside of the insertion part 17, and the like. Accordingly, the gas or water supplied from the air/water supply device (not illustrated) is injected from air/water supply nozzle (not illustrated) to the observation window 47 to wash the observation window 47.

The imaging device 48 has a condensing lens 52 and an imaging element 53 that are disposed along an optical path of the image light of the region to be observed, which has been incident from the observation window 47. The condensing lens 52 causes the image light of the region to be observed, which has been incident from the observation window 47, to be incident on an imaging surface of the imaging element 53.

The imaging element 53 is a complementary metal oxide semiconductor (CMOS) type or charge coupled device (CCD) type imaging element. The imaging element 53 images the image light of the region to be observed, which has been incident on the imaging surface through the condensing lens 52, (converts the image light into electrical signals), and outputs the image signals of the region to be observed to the overall control circuit 50. In addition, the imaging element 53 is provided with, for example, an oscillation unit 53*a* that outputs reference signals (clock signals) of a crystal oscillator or the like, and the imaging element 53 outputs the image signals with the reference signals oscillated from the oscillation unit 53*a* as references.

The magnetic field detection circuit 49 is electrically connected to the respective detection coils 25 within the insertion part 17. The magnetic field detection circuit 49 outputs the induced currents (induced electromotive forces), which are respectively generated in the respective detection coils 25 by the magnetic fields generated from the generation coils 39 of the magnetic field generator 13, to the overall control circuit 50 as the magnetic field detection data 55 equivalent to the magnetic field detection results by the respective detection coils 25. The magnetic field detection circuit 49 has a preamplifier 49*a* and an analog/digital (A/D) conversion circuit 49*b*.

The preamplifier 49*a* amplifies signals of the induced currents input from the respective detection coils 25, and outputs the signals to the A/D conversion circuit 49*b*. The A/D conversion circuit 49*b* converts amplification signal (analog signal) for the respective detection coils 25 into digital signals, and outputs the digital signals for the respective detection coils 25 to the overall control circuit 50 as the magnetic field detection data 55 for the respective detection coils 25.

The overall control circuit 50 is configured to include various arithmetic circuits including a central processing unit (CPU) and various memories, and performs overall control of the operation of the respective units of the endoscope 10. The overall control circuit 50 executes control programs stored in the memories (not illustrated), thereby functioning as a signal processing unit 57, a magnetic field detection control unit 58, and an image signal output unit 59.

The signal processing unit 57 performs various kinds of signal processing on the image signals output from the imaging element 53, and outputs a plurality of frame image signals 61, which are dynamic image data of the region to be observed, to the image signal output unit 59. The frame intervals of the respective frame image signals 61 are intervals corresponding to the reference signals oscillated by the aforementioned oscillation unit 53*a*.

The magnetic field detection control unit 58 acquires the magnetic field detection data 55 (induced current values) detected by the respective detection coils 25 via the magnetic field detection circuit 49, and outputs the magnetic field detection data 55 for the acquired respective detection coils 25 to the image signal output unit 59.

Figure 3:
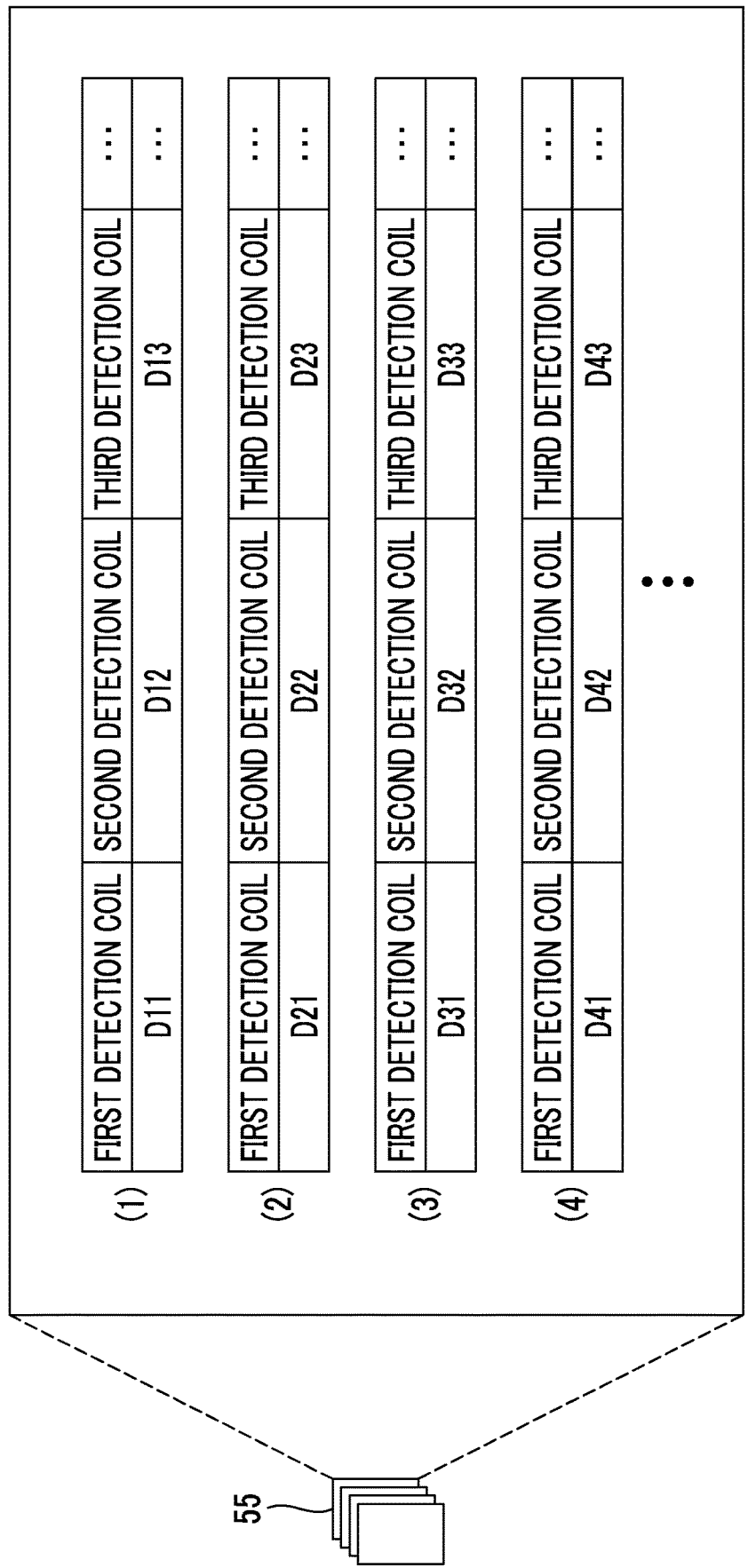
FIG. 3 is an explanatory view for explaining an example of magnetic field detection data output from a magnetic field detection control unit to an image signal output unit.

FIG. 3 is an explanatory view for explaining an example of the magnetic field detection data 55 output from the magnetic field detection control unit 58 to the image signal output unit 59. In the present embodiment, although described below in detail, switching control of the generation coils 39 that generate the magnetic fields in the magnetic field generator 13 is performed on the basis of frame start signals VD (refer to FIG. 4) for the respective frame image signals 61, that is, the reference signals from the oscillation unit 53a. Specifically, switching of generation coils 39 that generate magnetic fields during a period from one frame start signal VD to the next frame start signal VD (during one cycle of reference signals) is made to establish one cycle (refer to FIG. 5).

Thus, as illustrated in FIG. 3, the magnetic field detection control unit 58 repeatedly acquires the magnetic field detection data 55 from the respective detection coils 25 via the magnetic field detection circuit 49 whenever the respective generation coils 39 of the magnetic field generator 13 generate the magnetic fields at mutually different timings on the basis of the aforementioned reference signals [Numbers with parentheses in the drawing: refer to (1), (2), ... ]. That is, the magnetic field detection control unit 58 acquires the magnetic field detection data 55 of the respective detection coils 25 (a first detection coil, a second detection coil, ... ) for the respective generation coils 39.

Then, the magnetic field detection control unit 58 outputs the magnetic field detection data 55 (hereinafter simply referred to as the total magnetic field detection data 55) of the respective detection coils 25 for the acquired respective generation coils 39 to the image signal output unit 59. Accordingly, the total magnetic field detection data 55 is input from the magnetic field detection control unit 58 to the image signal output unit 59 in synchronization with the input of the frame image signals 61 from the signal processing unit 57 to the image signal output unit 59.

In addition, "D11 to D43, ... " in FIG. 3 represent the magnetic field detection data 55. For example, "D12" is magnetic field detection data 55 obtained by detecting a magnetic field, which is generated in a first generation coil 39, in a "second detection coil", and "D43" is magnetic field detection data 55 obtained by detecting a magnetic field, which is generated in a fourth generation coil 39, in a "third detection coil".

Figure 4:
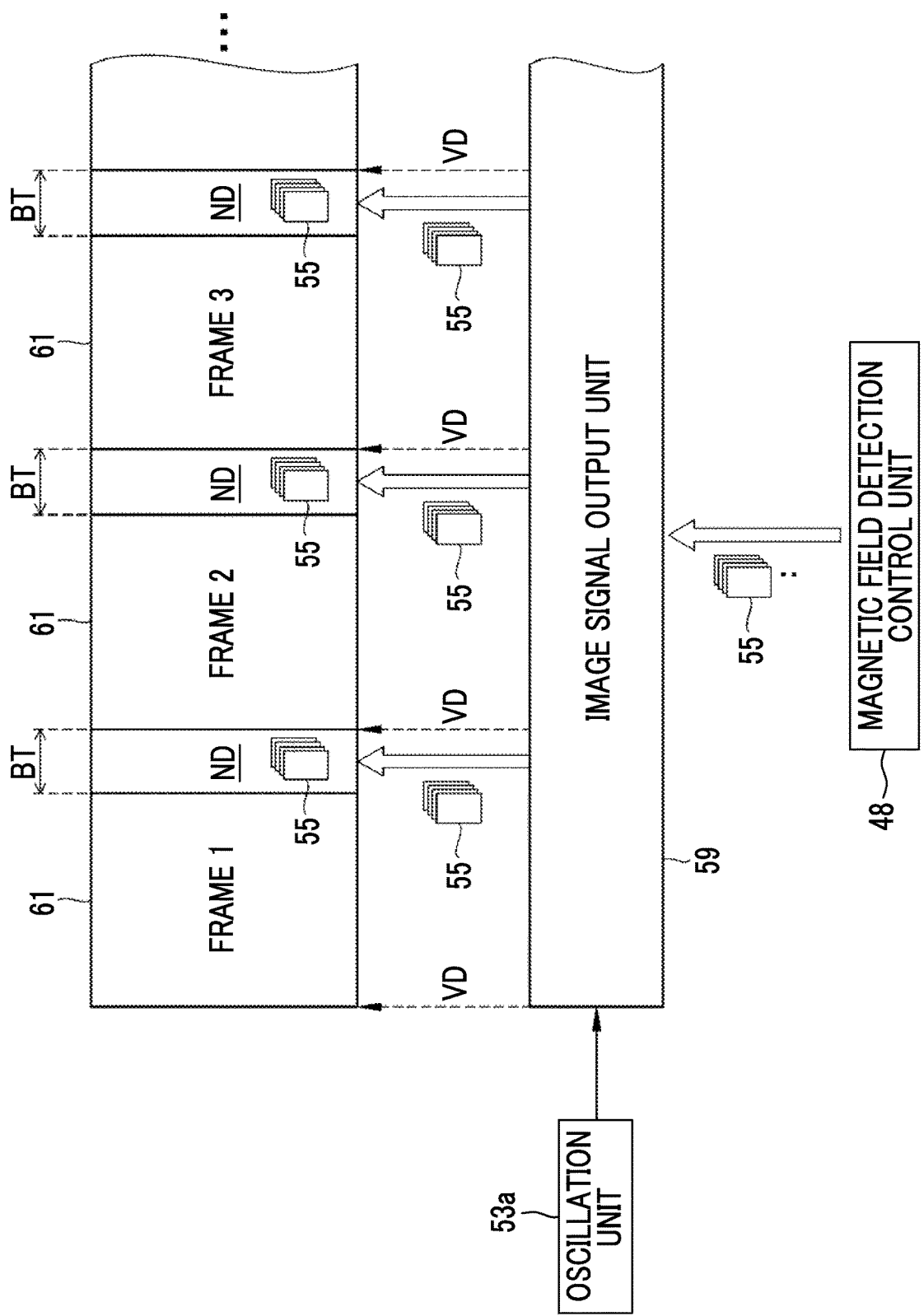
FIG. 4 is an explanatory view for explaining image output processing of frame image signals by the image signal output unit.

FIG. 4 is an explanatory view for explaining image output processing of the frame image signals 61 by the image signal output unit 59. As illustrated in FIG. 4, the image signal output unit 59 adds the frame start signals VD showing the start of the individual frame image signals 61 (the pause of the individual frame image signals 61) to the frame image signals 61 input from the signal processing unit 57 on the basis of the reference signals output from the oscillation unit 53a. Therefore, the frame start signals VD are signals synchronized with the reference signals. In addition, the signal processing unit 57 may perform the addition of the frame start signals VD to the frame image signals 61. In this case, the signal processing unit 57 also functions as the image signal output unit of the invention together with the image signal output unit 59.

Additionally, the image signal output unit 59 adds the total magnetic field detection data 55 input from the magnetic field detection control unit 58 in synchronization with the frame image signals 61, between the images of the frame image signals 61 input from the signal processing unit 57.

Specifically, the image signal output unit 59 adds the total magnetic field detection data 55 input from the magnetic field detection control unit 58 to a signal invalid region ND between frame image signals 61 corresponding to a blank time BT (perpendicular blank time) of the imaging element 53. That is, the image signal output unit 59 adds the total magnetic field detection data 55, which has been newly input from the magnetic field detection control unit 58, to a signal invalid regions ND between a frame image signal 61 newly input from the signal processing unit 57 to the image signal output unit 59, and the next frame image signal 61. Accordingly, the total magnetic field detection data 55 input from the magnetic field detection control unit 58 in synchronization with the frame image signals 61 can be added to the frame image signals 61 in one-to-one correspondence. As a result, the image signal output unit 59 can output the total magnetic field detection data 55 in synchronization with the frame image signals 61.

Referring back to FIG. 2, the image signal output unit 59 outputs the frame image signals 61, to which the frame start signals VD and the total magnetic field detection data 55 are added, to the earlier-described LD 36 via the signal cable 32. Accordingly, the optical signals obtained by converting the frame image signals 61 output from the image signal output unit 59 are transmitted toward the PD 37 of the light source device 11 from the LD 36. In addition, the frame image signals 61 to which the frame start signals VD and the total magnetic field detection data 55 are added, that is, the frame image signals 61 output from the image signal output unit 59, are equivalent to added image signals and added frame image signals of the invention.

<Light Source Device>

The light source device 11 has an illumination light source 63, the aforementioned PD 37, a communication interface 65, and a light source control unit 64. The illumination light source 63 is, for example, a semiconductor light source, such as an LD or a light emitting diode (LED), and emits white light having a wavelength ranging from a red region to a blue region as the illumination light. In addition, the type of illumination light source 63 is not particularly limited. The illumination light emitted from the illumination light source 63 is incident on the incident end of the aforementioned light guide 33.

The PD 37 receives the optical signals transmitted from the LD 36. After the optical signals received by the PD 37 are converted into the original frame image signals 61 that are electrical signals, the converted frame image signals 61' are input to the light source control unit 64.

The light source control unit 64 is configured to include the various arithmetic circuits including the (CPU) and the various memories, and performs overall control of the operation of the respective units of the light source device 11, such as the illumination light source 63 and the PD 37. Additionally, the light source control unit 64 outputs the converted frame image signals 61 input from the PD 37, to the navigation device 12 via the communication interface 65.

<Navigation Device>

The navigation device 12 has an image signal acquisition unit 68, a signal detection unit 69, a timing generator (TG) 70, a magnetic field generation control unit 71, a position detection unit 72, an insertion part shape detection unit 73, and a display output unit 74. In addition, the "navigation" referred to here is enable the operator to ascertain the shape of the insertion part 17 of the endoscope 10 within the subject, the position of the distal end part 23 of the insertion part 17, and the like. Additionally, the respective units of the navigation device 12 are constituted of various arithmetic circuits (not illustrated) including one or a plurality of CPUs, and are operated by executing control programs stored in memories (not illustrated).

The image signal acquisition unit 68 serially acquires the frame image signals 61 from the light source control unit 64 via the communication interface 65. Then, the image signal acquisition unit 68 serially outputs the acquired frame image signals 61 and the like to the display output unit 74. In addition, the signal detection unit 69 and the position detection unit 72 to be described below respectively make an access to the frame image signals 61 acquired by the image signal acquisition unit 68, and acquire required information (the frame start signals VD and the total magnetic field detection data 55).

The signal detection unit 69 serially detects (extracts) the frame start signals VD from the frame image signals 61 newly acquired by the image signal acquisition unit 68, and serially outputs the detected frame start signals VD to the TG 70. As earlier described, the frame start signals VD are signals synchronized with the reference signals oscillated from the oscillation unit 53a. Then, switching control of the generation coils 39 that generate the magnetic fields in the magnetic field generator 13 is performed on the basis of the frame start signals VD by the TG 70 and the magnetic field generation control unit 71 (refer to FIG. 5).

Figure 5:
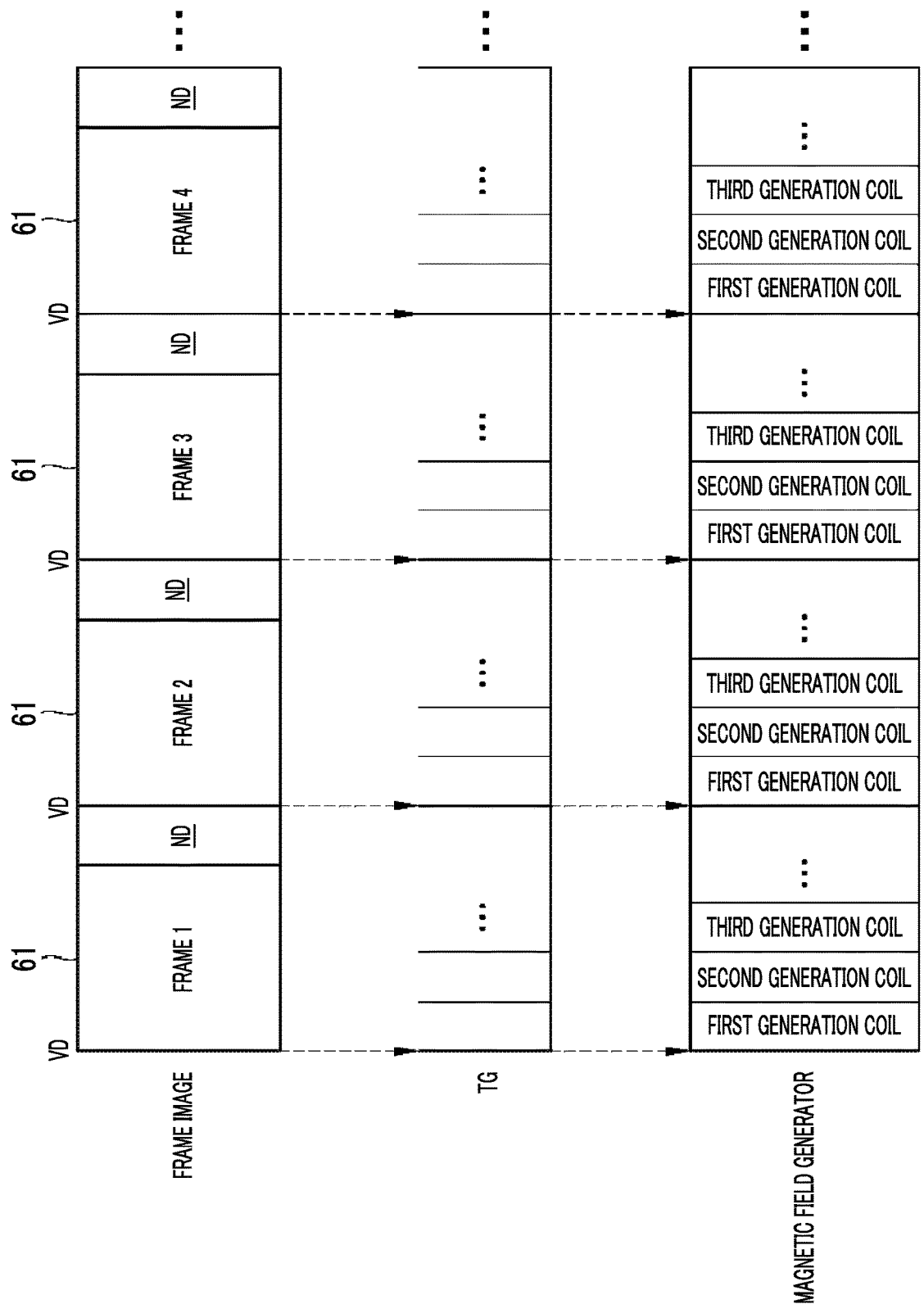
FIG. 5 is an explanatory view for explaining switching control of generation coils of the first embodiment.

FIG. 5 is an explanatory view for explaining the switching control of the generation coils 39 of the first embodiment. As illustrated in FIG. 5, the TG 70 outputs the clock signals for the switching control of the respective generation coils 39 to the magnetic field generation control unit 71 on the basis of the frame start signals VD input from the signal detection unit 69. The clock frequencies of the clock signals are set to frequencies required for establishing a switching cycle of the generation coils 39 that generate the magnetic fields between the frame start signals VD.

The magnetic field generation control unit 71 sequentially applies driving currents in predetermined order to the respective generation coils 39 (the first generation coil, the second generation coil, . . . ) of the magnetic field generator 13 on the basis of the clock signals input from the TG 70, and switches the generation coils 39 that generate the magnetic fields. Accordingly, the switching control of the generation coils 39 that generate the magnetic fields is performed with the frame start signals VD, that is, the aforementioned reference signals as references. Additionally, a switching cycle of the generation coils 39 that generate the magnetic fields is established between the frame start signals VD.

In addition, information on the frequencies of the clock signals output from the TG 70 is input to the earlier described magnetic field detection control unit 58 (refer to FIG. 2). For this reason, the magnetic field detection control unit 58 repeatedly acquires the magnetic field detection data 55 from the respective detection coils 25 via the magnetic field detection circuit 49, at frequencies corresponding to the clock signals output from the TG 70 with the aforementioned reference signals as references. Accordingly, the switching control of the generation coils 39 that generate the magnetic fields in the magnetic field generator 13, and the detection of the total magnetic field detection data 55 in the endoscope 10 and the addition of the total magnetic field detection data 55 to the signal invalid regions ND are synchronously performed with the frame start signals VD (reference signals) as references.

Referring back to FIG. 2, the position detection unit 72 serially detects (extracts) the frame start signals VD and the total magnetic field detection data 55 for the respective frame image signals 61 newly acquired by the image signal acquisition unit 68 and the respective signal invalid regions ND, and detects the positions of the respective detection coils 25 on the basis of the detected frame start signals VD and total magnetic field detection data 55. The position detection unit 72 is provided with a determination unit 72a that determines a correspondence relationship 75 (refer to FIG. 6) of the generation coils 39 that have generated the magnetic fields, and respective items of the total magnetic field detection data 55. Then, the position detection unit 72 detects the positions of the respective detection coils 25 on the basis of the determination results of the determination unit 72a.

Figure 6:
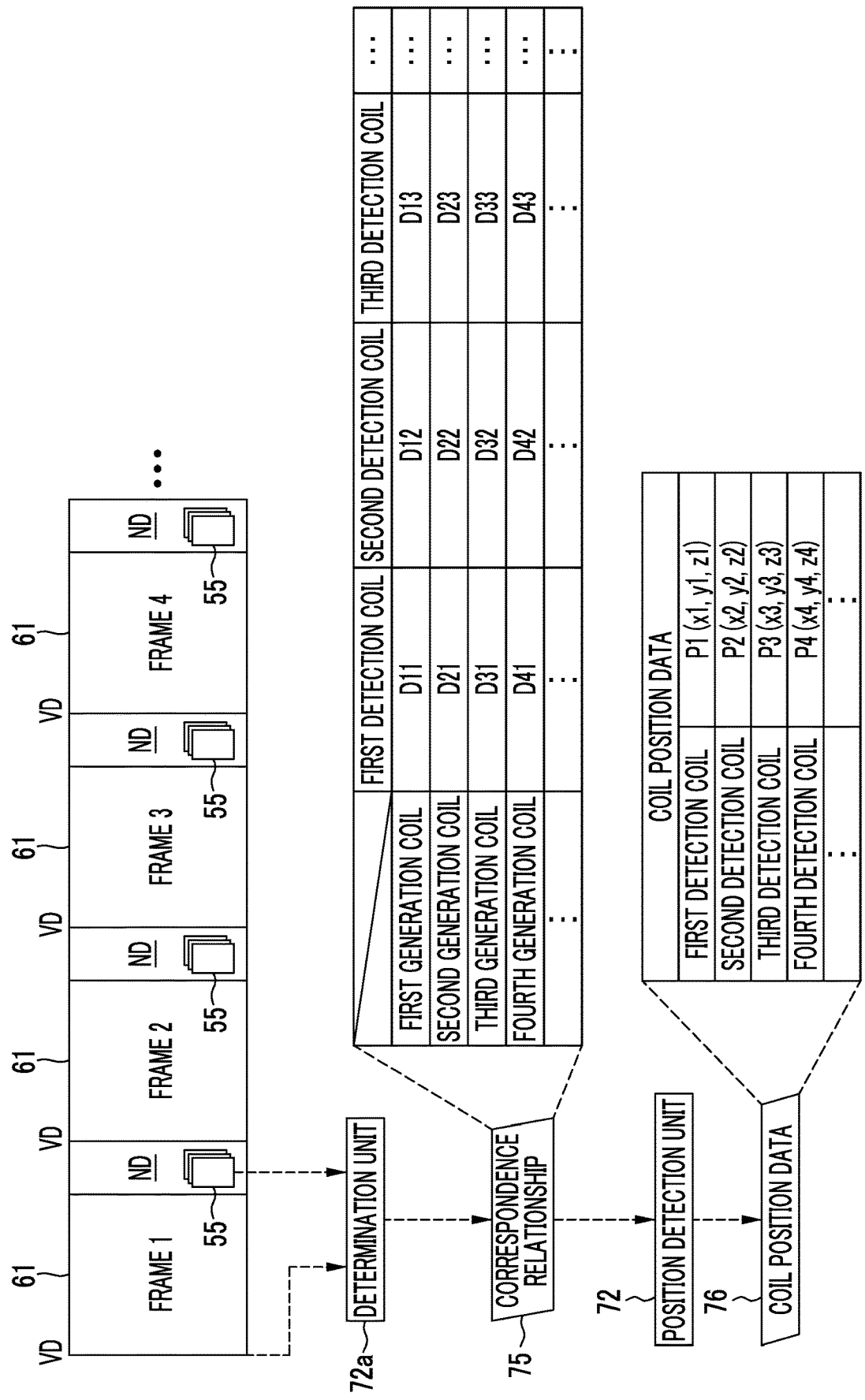
FIG. 6 is an explanatory view for explaining determination processing by a determination unit, and position detection processing of respective detection coils by a position detection unit.

FIG. 6 is an explanatory view for explaining determination processing by the determination unit 72a, and position detection processing of the respective detection coils 25 by the position detection unit 72. As illustrated in FIG. 6, the determination unit 72a determines the correspondence relationship 75 between the respective generation coils 39 (the first generation coil, the second generation coil, . . . ), and the total magnetic field detection data 55 (D11 to D43, . . . ) detected from the signal invalid regions ND, on the basis of the frame start signals VD detected from the frame image signals 61.

Specifically, in the present embodiment, the switching control (refer to FIG. 5) of the generation coils 39 that generate the magnetic fields, and the acquisition (refer to FIG. 3) of the magnetic field detection data 55 for the respective generation coils 39 are performed with the frame start signals VD (reference signals) as references. For this reason, in a case where the switching order (refer to FIG. 5) of the generation coils 39 having the frame start signals VD as references is known, the determination unit 72a can determine the generation coils 39 corresponding to the respective items of the total magnetic field detection data 55. That is, the determination unit 72a can determine the correspondence relationship 75 on the basis of the frame start signals VD. For this reason, the frame start signals VD function as specification information of the invention.

Figure 7:
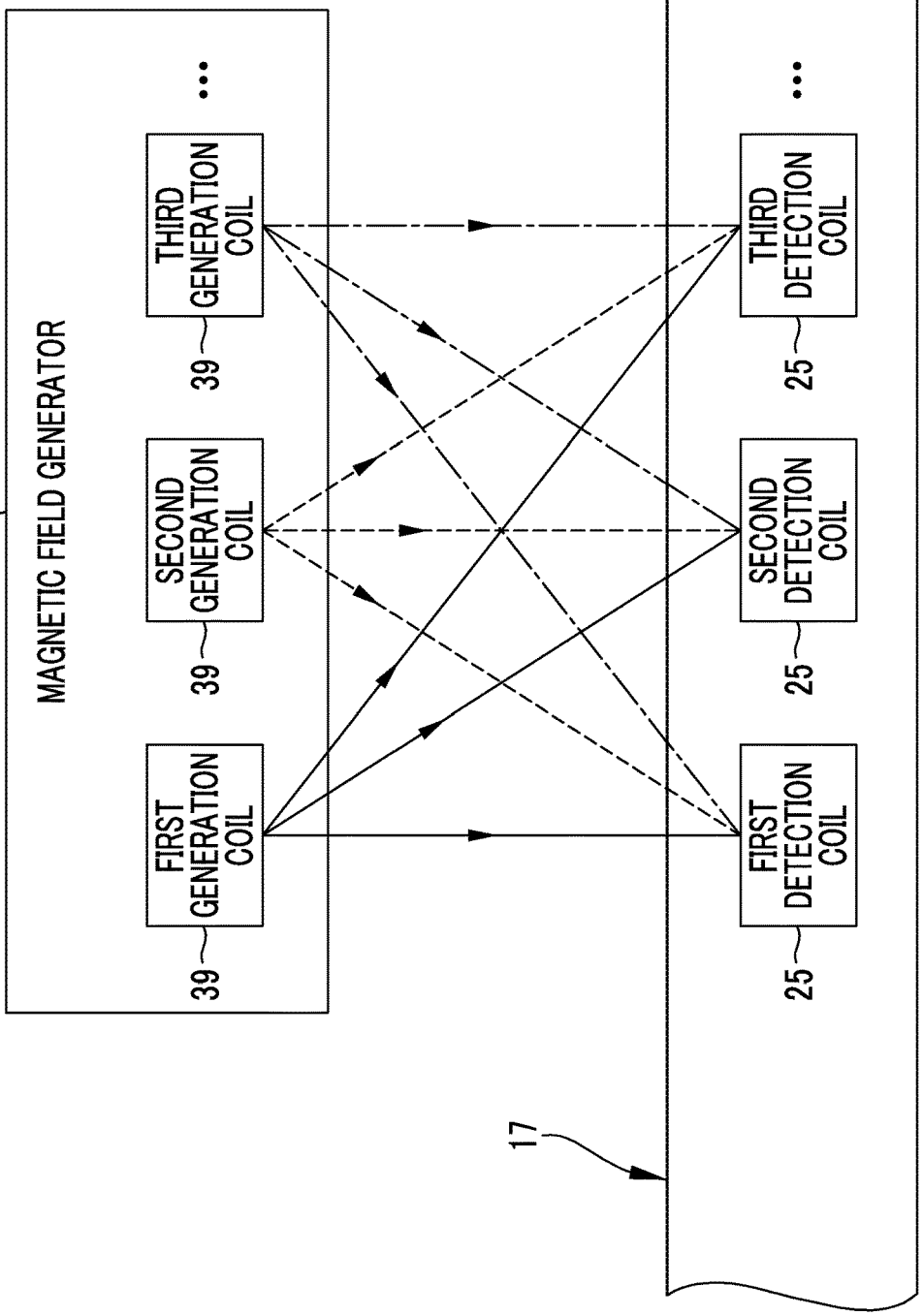
FIG. 7 is an explanatory view of the principle of the position detection processing of the respective detection coils by the position detection unit.

FIG. 7 is an explanatory view of the principle of the position detection processing of the respective detection coils 25 by the position detection unit 72. As illustrated in FIG. 7, the magnetic field detection data 55 (induced currents), which are respectively detected in the respective detection coils 25, varies in correspondence with distances between the generation coils 39 that have generated the magnetic fields, and the respective detection coils 25. For this reason, the positions of the respective detection coils 25 can be detected on the basis of the magnetic field detection data 55 obtained by detecting the magnetic fields, which are generated in the respective generation coils 39, with the respective detection coils 25, respectively. In addition, since specific detection methods of the positions of the respective detection coils 25 are well-known techniques, the description thereof will be omitted herein.

Referring back to FIG. 6, the position detection unit 72 detects coil position data 76 showing position detection results (P1, P2, . . . ) of the respective detection coils 25, on the basis of the correspondence relationship 75 determined by the determination unit 72a, and the total magnetic field detection data 55. In addition, the positions of the respective detection coils 25 are, for example, relative positions with the magnetic field generator 13 as a reference, and are three-dimensional coordinates according to the XYZ coordinate axes of the aforementioned orthogonal coordinate system XYZ (refer to FIG. 1). Then, the position detection unit 72 outputs the detected coil position data 76 to the insertion part shape detection unit 73 (refer to FIG. 2).

In addition, the position detection unit 72 repeatedly performed the determination processing by the aforementioned determination unit 72a, and the position detection processing of detecting the coil position data 76 of the respective detection coils 25, whenever the image signal acquisition unit 68 acquires new frame image signals 61.

Referring back to FIG. 2, the insertion part shape detection unit 73 detects the shape of the insertion part 17 within the subject on the basis of the coil position data 76 input from the position detection unit 72.

Figure 8:
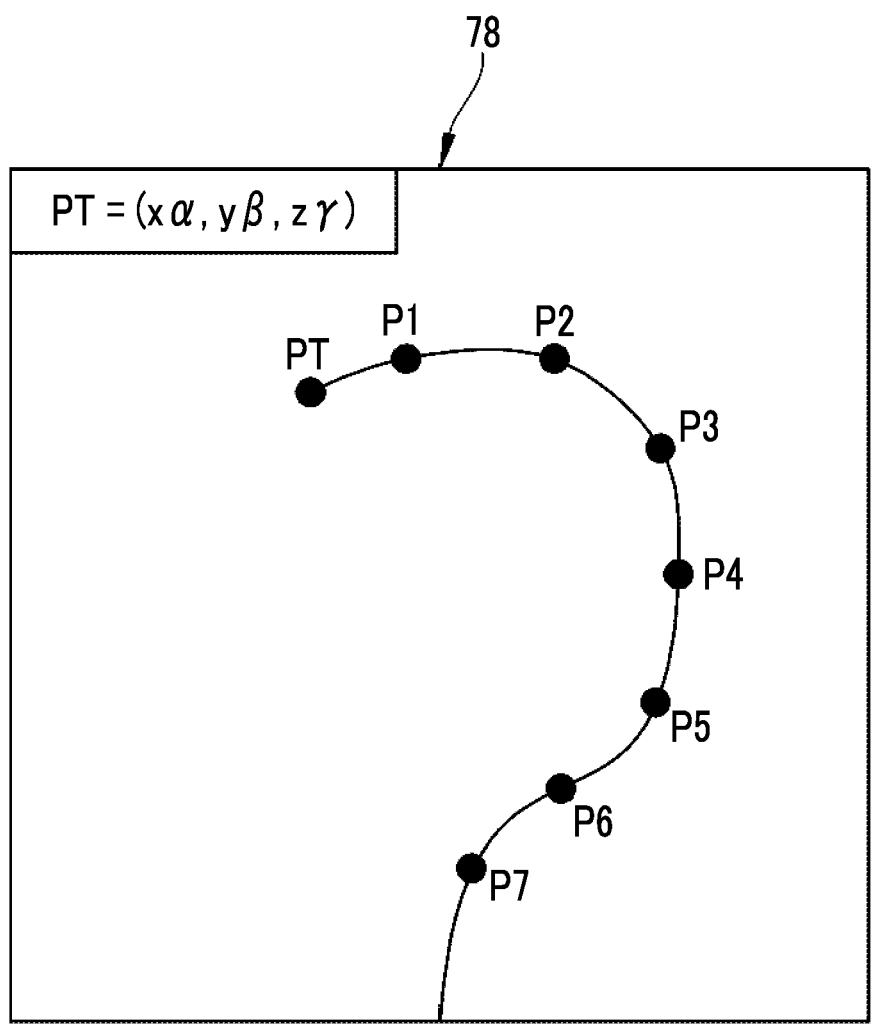
FIG. 8 is an explanatory view for explaining an example of shape detection processing of an insertion part by an insertion part shape detection unit.

FIG. 8 is an explanatory view for explaining an example of the shape detection processing of the insertion part 17 by the insertion part shape detection unit 73. As illustrated in FIG. 8, the insertion part shape detection unit 73 performs the fitting processing or the like of interpolating respective positions by using an appropriate curve, on the basis of the positions (P1, P2, . . . ) of the respective detection coils 25 indicated by the coil position data 76, and creates insertion part shape data 78 showing shape detection results of the insertion part 17. In addition, the shape detection methods of the insertion part 17 based on the coil position data 76 are well-known technique, and the shape detection methods are not particularly limited. Although the insertion part shape data 78 showing the two-dimensional shape of the insertion part 17 is described as an example in the drawing, for example, data showing a three-dimensional shape may be adopted, and the expression form of the shape of the insertion part 17 is also not particularly limited.

Moreover, the insertion part shape detection unit 73 detects a distal end position PT of the distal end part 23 of the insertion part 17 on the basis of the coil position data 76, and adds a detection result of the distal end position PT to the insertion part shape data 78. In addition, the distal end position PT is expressed by, for example, a relative position having the magnetic field generator 13 as a reference. Accordingly, the distal end position PT of the distal end part 23 can be determined together with the shape of the insertion part 17 within the subject.

The insertion part shape detection unit 73 outputs the insertion part shape data 78 to the display output unit 74 (refer to FIG. 2). In addition, creation and output of the insertion part shape data 78 by the insertion part shape detection unit 73 are repeatedly executed whenever new coil position data 76 is input from the position detection unit 72.

Referring back to FIG. 2, the display output unit 74 outputs the frame image signals 61, which have been previously input from the aforementioned image signal acquisition unit 68, and the insertion part shape data 78 input from the insertion part shape detection unit 73, to the processor 14 via communication interfaces 80A and 80B. In this case, the display output unit 74 associates the frame image signals 61 with the insertion part shape data 78 created on the basis of the total magnetic field detection data 55 and the like synchronized with the frame image signals 61, and outputs the associated signals to the processor 14.

<Processor>

The processor 14 has a display input unit 82 and a display control unit 83. The display input unit 82 serially outputs the frame image signals 61 and the insertion part shape data 78, which are serially input via the communication interfaces 80A and 80B from the display output unit 74, to the display control unit 83.

The display control unit 83 receives the input of the frame image signals 61 and the insertion part shape data 78 from the display input unit 82, and displays the observation image 41 (dynamic image) based on the frame image signals 61 and the insertion part shape image 42 based on the insertion part shape data 78 on the monitor 15 (refer to FIG. 1).

[Action of Endoscope System of First Embodiment]

Figure 9:
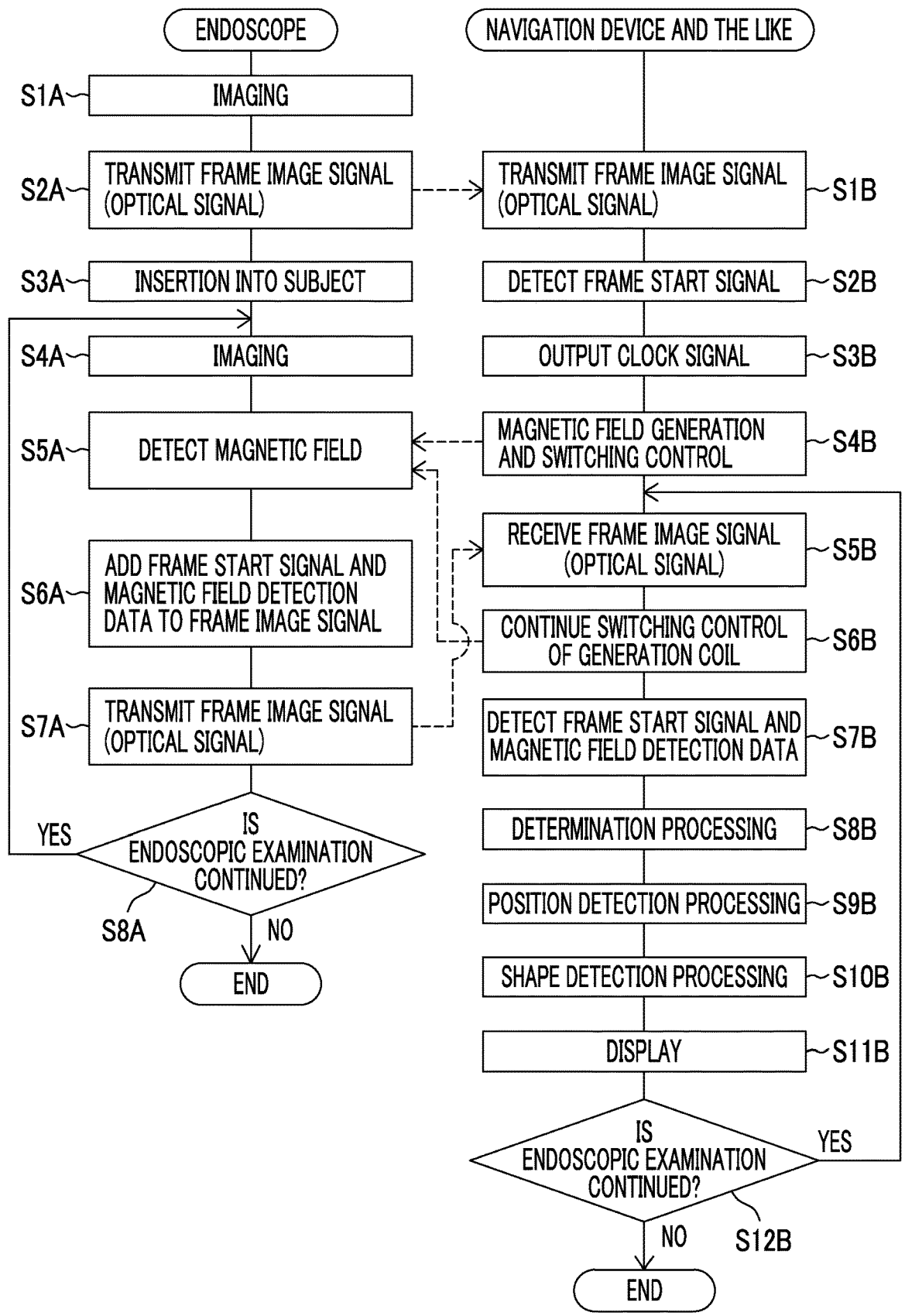
FIG. 9 is a flowchart illustrating a flow of endoscopic examination in the endoscope system of the first embodiment, especially, display processing of an observation image and an insertion part shape image.

Next, the action of the endoscope system 9 of the first embodiment will be described with reference to FIG. 9. In addition, FIG. 9 is a flowchart showing a flow of endoscopic examination in the endoscope system 9 of the first embodiment, especially, display processing (navigation method) of the observation image 41 and the insertion part shape image 42.

The imaging element 53 images the image light incident through the observation window 47 and the condensing lens 52 after startup of the respective units of the endoscope system 9. Accordingly, the imaging element 53 serially outputs the image signals to the signal processing unit 57 on the basis of the reference signals oscillated from the oscillation unit 53a (Step S1A). The image signals input from the imaging element 53 to the signal processing unit 57 are output to the image signal output unit 59 as the frame image signals 61 after being subjected to various kinds of signal processing in the signal processing unit 57, and are output to the LD 36 after the frame start signals VD are further added in the image signal output unit 59.

The LD 36 transmits the optical signals, which are obtained by converting the frame image signals 61 input from the image signal output unit 59, toward the PD 37 of the light source device 11 (Step S2A).

The optical signals transmitted from the LD 36 are received in the PD 37 of the light source device 11, are converted into the original frame image signals 61 that are electrical signals, and are then output to the image signal acquisition unit 68 of the navigation device 12 via the light source control unit 64 and the communication interface 65 (Step S1B).

In a case where the image signal acquisition unit 68 acquires the frame image signals 61, the signal detection unit 69 detects frame start signals VD from the frame image signals 61 acquired by the image signal acquisition unit 68, and outputs the detected frame start signals VD to the TG 70 (Step S2B). Thereafter, whenever the image signal acquisition unit 68 acquires the new frame image signals 61, the detection and output of the frame start signals VD by the signal detection unit 69 are repeatedly executed.

The TG 70, which has received the input of the frame start signals VD, outputs the clock signals having the frame start signals VD as references to the magnetic field generation control unit 71 as illustrated in FIG. 5 earlier described (Step S3B). Then, the magnetic field generation control unit 71, which has received the input of the clock signals from the TG 70, causes the magnetic fields to be generated at different timings from the respective generation coils 39 on the basis of the clock signals. Accordingly, the switching control of the respective generation coils 39 having the frame start signals VD (reference signals) as references is performed, and the switching of the generation coils 39 that generate the magnetic fields between the frame start signals VD establish one cycle (Step S4B; equivalent to a magnetic field generation control step of the invention). The startup of the endoscope system 9 is completed by the processing up to the above Step S4B.

Next, the insertion part 17 of the endoscope 10 is inserted into the subject (into a body cavity of a patient) (Step S3A), and imaging of the region to be observed within the subject is started. The illumination light supplied from the illumination light source 63 of the light source device 11 is emitted toward the region to be observed through the light guide 33 and the irradiation lens 45 from the illumination window 46. Additionally, the imaging element 53 images the image light of the region to be observed that is incident through the observation window 47 and the condensing lens 52, and serially outputs the image signals to the signal processing unit 57 with the aforementioned reference signals as references (Step S4A). Accordingly, the image signals output from the imaging element 53 are subjected to the respective kinds of signal processing in the signal processing unit 57, and are serially output to the image signal output unit 59 as the frame image signals 61.

Additionally, the magnetic field detection control unit 58 of the endoscope 10 controls the magnetic field detection circuit 49 at the frequencies corresponding to the clock signals of the TG 70, on the basis of the reference signals oscillated from the oscillation unit 53a, and repeatedly acquires the magnetic field detection data 55 detected by the respective detection coils 25 (Step S5A). That is, the acquisition of the magnetic field detection data 55 of the respective detection coils 25 by the magnetic field detection control unit 58 is performed in synchronization with the switching control of the generation coils 39 in the magnetic field generator 13. The, the magnetic field detection control unit 58 outputs the total magnetic field detection data 55 of the respective detection coils 25 for the respective generation coils 39 to the image signal output unit 59 in synchronization with the input of the frame image signals 61 from the signal processing unit 57 to the image signal output unit 59.

The image signal output unit 59 adds the frame start signals VD to the frame image signals 61 input from the signal processing unit 57 and adds the total magnetic field detection data 55 to the signal invalid regions ND between the respective frame image signals 61, as illustrated in FIG. 4 as earlier described (Step S6A). Accordingly, the image signal output unit 59 can add the total magnetic field detection data 55, which has been input from the magnetic field detection control unit 58 in synchronization with the frame image signals 61, to the frame image signals 61 in one-to-one correspondence.

Next, the image signal output unit 59 outputs the frame image signals 61, to which the frame start signals VD and the total magnetic field detection data 55 are added, to the LD 36 via the signal cable 32. Then, the LD 36, which has received the input of the frame image signals 61 from the image signal output unit 59, transmits the optical signals obtained by converting the frame image signals 61, toward the PD 37 (Step S7A).

The optical signals transmitted from the LD 36 are received in the PD 37 of the light source device 11, are converted into the original frame image signals 61 that are electrical signals, and are then output to the image signal acquisition unit 68 of the navigation device 12 via the light source control unit 64 and the like (Step S5B; equivalent to an image signal acquisition step of the invention).

The image signal acquisition unit 68, which has acquired the newly output frame image signals 61 from the light source control unit 64, outputs the frame image signals 61 to the display output unit 74. In this case, by repeatedly executing the processing from Step S2B to Step S4B as earlier described to the frame image signals 61 newly acquired the image signal acquisition unit 68, the switching control of the respective generation coils 39 in the magnetic field generator 13 are consecutively performed (equivalent to Step S6B; the magnetic field generation control step of the invention).

Additionally, the position detection unit 72 detects the frame start signals VD and the total magnetic field detection data 55 from the frame image signals 61 newly acquired by the image signal acquisition unit 68, and the signal invalid regions ND (Step S7B). Then, as illustrated in FIG. 6 as earlier described, the determination unit 72a performs the determination processing of determining the correspondence relationship 75 between the respective generation coils 39 and the total magnetic field detection data 55 on the basis of the frame start signals VD (Step S8B).

Next, the position detection unit 72 performs the position detection processing of detecting the coil position data 76 showing the positions of the respective detection coils 25 from the previously detected total magnetic field detection data 55, on the basis of the correspondence relationship 75 determined by the determination unit 72a determined (Step S9B; equivalent to a position detection step of the invention). The coil position data 76 detected by the position detection processing is output to the insertion part shape detection unit 73 from the position detection unit 72.

The insertion part shape detection unit 73, which has received the input of the coil position data 76, performs the shape detection processing of the insertion part 17 to create the insertion part shape data 78 as illustrated in FIG. 8 as earlier described, on the basis of the coil position data 76 (Step S10B). Additionally, the insertion part shape detection unit 73 detects the distal end position PT of the distal end part 23 on the basis of the coil position data 76, and adds the detection result of the distal end position PT to the insertion part shape data 78. Then, the insertion part shape detection unit 73 outputs the insertion part shape data 78 to the display output unit 74.

The display output unit 74, which has received the input of the insertion part shape data 78, outputs the insertion part shape data 78, and the frame image signals 61 previously input from the image signal acquisition unit 68, to the processor 14 via the communication interfaces 80A and 80B. Accordingly, the frame image signals 61, and the insertion part shape data 78 created on the basis of the total magnetic field detection data 55 synchronized with the frame image signals 61 can be associated with each other, and the associated signals can be output to the processor 14.

The frame image signals 61 and the insertion part shape data 78, which have been input from the display output unit 74 to the display input unit 82 of the processor 14, are output to the monitor 15 by the display control unit 83. Accordingly, the observation image 41 (dynamic image) based on the frame image signals 61 and the insertion part shape image 42 based on the insertion part shape data 78 are displayed on the monitor 15 (Step S11B). By referring to the insertion part shape image 42 displayed on the monitor 15, the operator can ascertain the shape of the insertion part 17 within the subject, and distal end position PT of the distal end part 23.

Thereafter, the processing from the aforementioned Steps S4A to S7A is repeatedly executed until the endoscopic examination is completed, and the frame image signals 61 to which the frame start signals VD and the total magnetic field detection data 55 are added are serially output from the endoscope 10 via the light source device 11 to the navigation device 12 (Step S8A). Additionally, in accordance therewith, the processing from the aforementioned Steps S5B to S11B is repeatedly executed in the navigation device 12, the processor 14, and the like, and the switching control of the generation coils 39 and the display of the observation image 41 and the insertion part shape image 42 are consecutively performed (Step S12B).

Effects of First Embodiment

In the endoscope system 9 of the above first embodiment, the frame image signals 61 to which the frame start signals VD and the total magnetic field detection data 55 are added is output from the endoscope 10 to the navigation device 12. Thus, it is unnecessary to separately provide the endoscope 10 with an output system for outputting the total magnetic field detection data 55 to the navigation device 12. As a result, the total magnetic field detection data 55 can be output to the navigation device 12 at low costs without enlarging the endoscope 10. That is, it is possible to reduce the size of the endoscope 10 and reduce the cost thereof.

Additionally, by synchronously performing the switching control of the generation coils 39 in the magnetic field generator 13 and the detection of the total magnetic field detection data 55 in the endoscope 10 and the addition of the total magnetic field detection data 55 to the frame image signal 61, with the frame start signals VD (reference signals) as references, in the navigation device 12, the aforementioned correspondence relationship 75 can be determined on the basis of the frame start signals VD detected from the frame image signals 61. As a result, the positions of the respective detection coils 25 can be detected, and the shape and the distal end position PT of the insertion part 17 within the subject can be obtained.

Moreover, the shape and the distal end position PT of the insertion part 17 within the subject can be ascertained for the respective frame image signals 61 by performing the detection of the total magnetic field detection data 55 and the addition of the total magnetic field detection data 55 to the frame image signals 61 on the basis of the frame start signals VD (reference signals). Accordingly, the shape and the distal end position PT of the insertion part 17 in a case where the respective frame image signals 61 are obtained can be confirmed later.

Endoscope System of Second Embodiment

In the above first embodiment, the switching control of the generation coils 39 by the magnetic field generation control unit 71 is performed such that switching of the respective generation coils 39 establishes one cycle between the frame start signals VD (refer to FIG. 5). However, the respective generation coils 39 may be switched in synchronization with the frame start signals VD.

Figure 10:
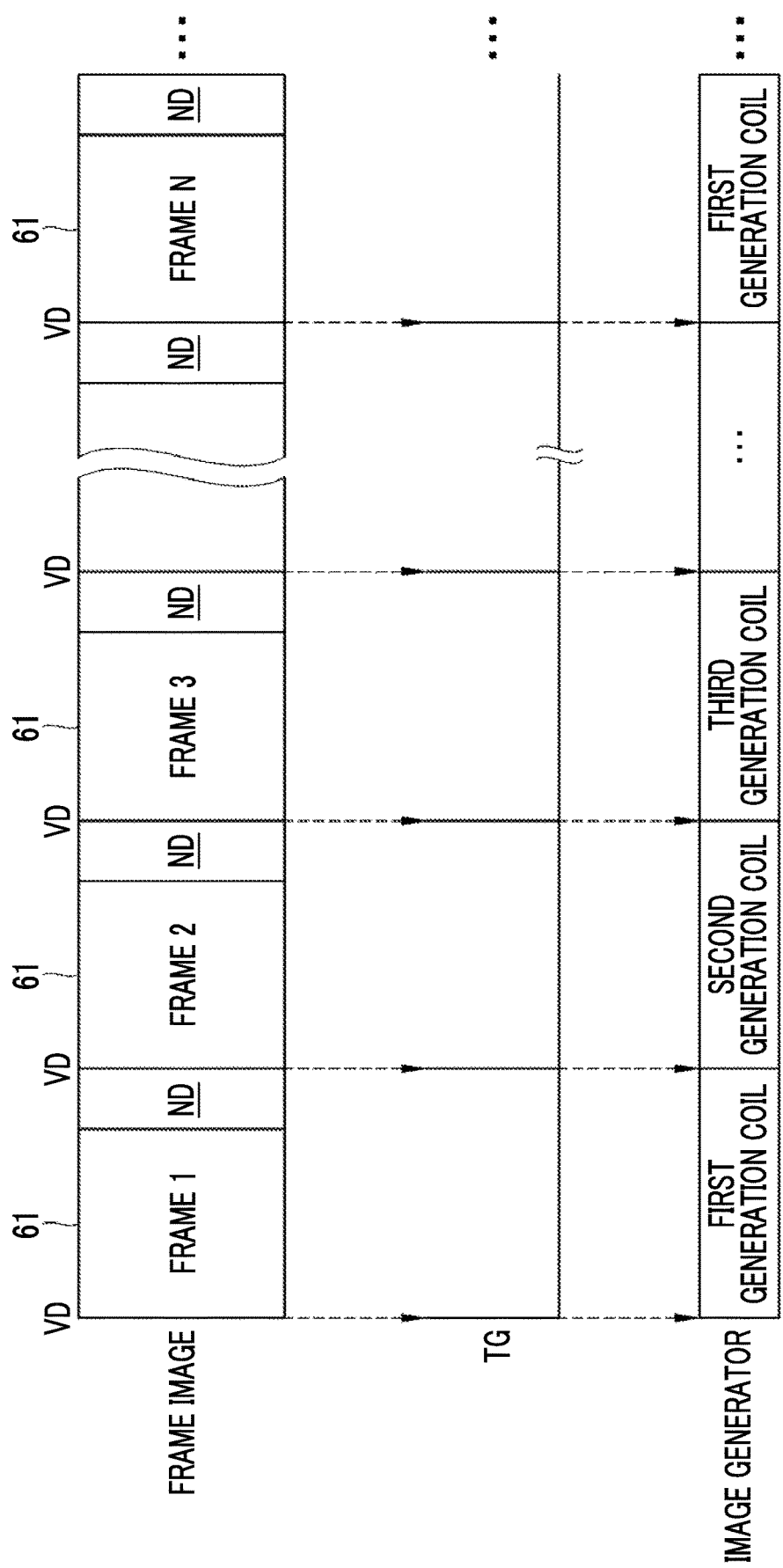
FIG. 10 is an explanatory view for explaining a switching control of generation coils in an endoscope system of a second embodiment.

FIG. 10 is an explanatory view for explaining the switching control of the generation coils 39 in the endoscope system 9 of a second embodiment. In addition, the endoscope system 9 of the second embodiment has basically the same configuration as that of the above first embodiment except that the switching control of the generation coils 39 is different from that of the above first embodiment. For this reason, components having the same functions and configurations as those of the above first embodiment will be designated by the same reference signs, and the description thereof will be omitted.

As illustrated in FIG. 10, the TG 70 of the second embodiment outputs the clock signals to the magnetic field generation control unit 71 whenever the frame start signals VD are input from the signal detection unit 69. Then, the magnetic field generation control unit 71 sequentially applies the driving currents in predetermined order to the respective generation coils 39 of the magnetic field generator 13 on the basis of the clock signals input from the TG 70, and switches the generation coils 39 that generate the magnetic fields. Accordingly, the switching control of the generation coils 39 is performed in synchronization with the frame start signals VD.

Additionally, the magnetic field detection control unit 58 of the second embodiment repeatedly acquires the magnetic field detection data 55 from the respective detection coils 25 via the magnetic field detection circuit 49 in synchronization with the aforementioned reference signals. Accordingly, also in the second embodiment, the switching control of the generation coils 39 that generate the magnetic fields in the magnetic field generator 13, and the detection of the total magnetic field detection data 55 in the endoscope 10 and the addition of the total magnetic field detection data 55 to the frame image signals 61 are synchronously performed with the frame start signals VD (reference signals) as references. Also, In the second embodiment, the magnetic field detection data 55 obtained by detecting a magnetic field generated in any of the respective generation coils 39 with each detection coil 25 is added to each signal invalid region ND.

Figure 11:
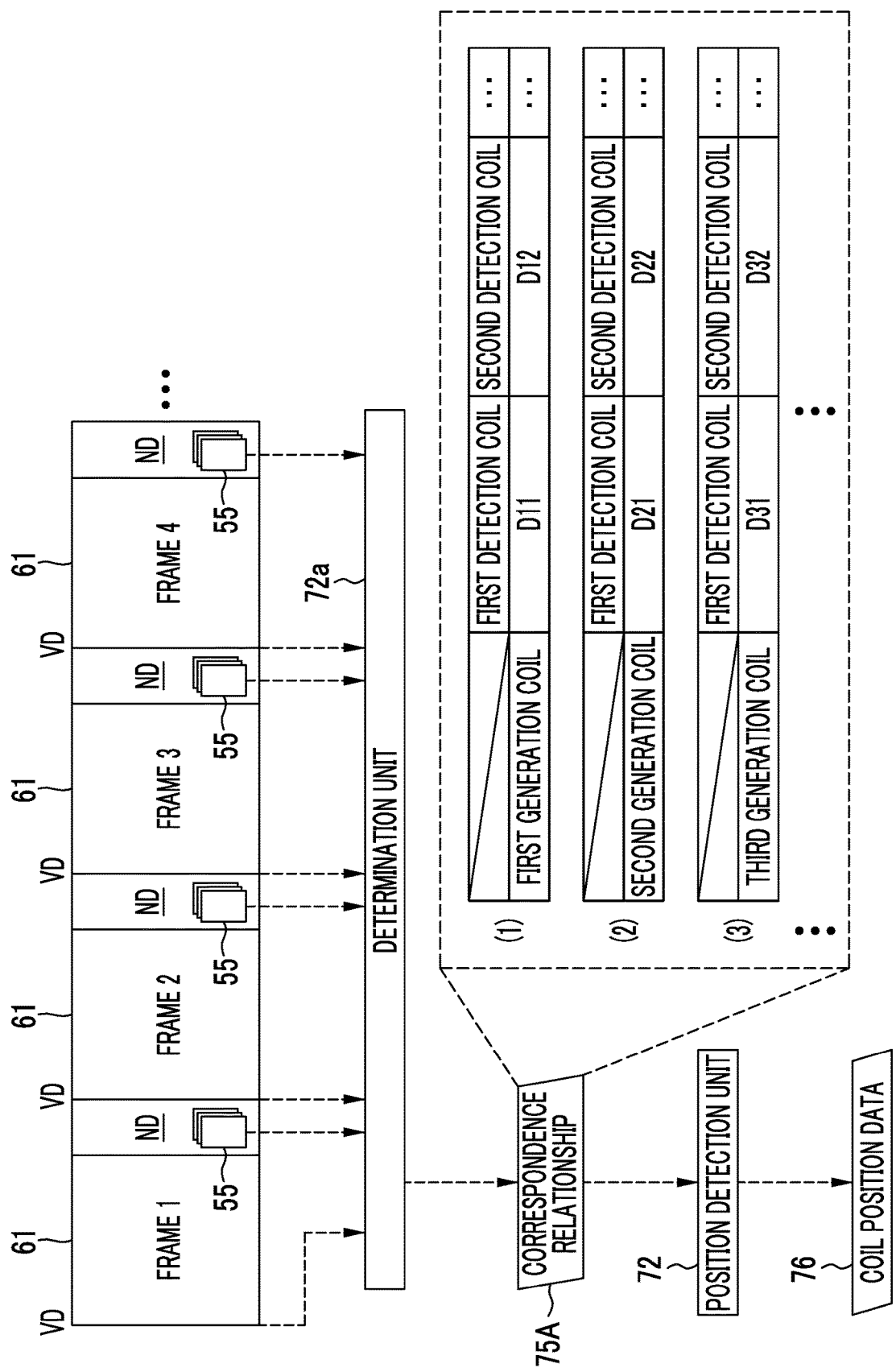
FIG. 11 is an explanatory view for explaining determination processing by a determination unit and position detection processing of respective detection coils by a position detection unit in the second embodiment.

FIG. 11 is an explanatory view for explaining the determination processing by the determination unit 72a of the second embodiment, and the position detection processing of the respective detection coils 25 by the position detection unit 72. In the above first embodiment, since the total magnetic field detection data 55 is added to the respective signal invalid regions ND, the coil position data 76 of the respective detection coils 25 can be detected for the respective frame image signals 61 (that is, in units of frames). In contrast, in the second embodiment, the magnetic field detection data 55 of each detection coil 25 corresponding to any of the respective generation coils 39 is added to each signal invalid region ND. Therefore, the coil position data 76 of the respective detection coils 25 is detected in units of a plurality of frame image signals 61 (that is, in units of a plurality of frames).

As illustrated in FIG. 11, the determination unit 72a of the second embodiment determines the generation coils 39 corresponding to the magnetic field detection data 55 of the respective detection coils 25, as illustrated by numbers with parentheses [(1), (2), . . . ] in the drawing, whenever the position detection unit 72 detects the frame start signals VD and the magnetic field detection data 55 of the respective detection coils 25. The switching order of the generation coils 39 having the frame start signals VD (reference signals) as references is known (refer to FIG. 10). Thus, also in the determination unit 72a of the second embodiment, the generation coils 39 corresponding to the magnetic field detection data 55 of the respective detection coils 25 can be determined on the basis of the frame start signals VD. Accordingly, the determination unit 72a can sequentially determine a correspondence relationship 75A between the magnetic field detection data 55 of the respective detection coils 25, and the plurality of generation coils 39.

Next, the position detection unit 72 of the second embodiment performs the position detection processing of detecting the aforementioned coil position data 76 by basically the same method as that of the above first embodiment, on the basis of the correspondence relationship 75A determined by the determination unit 72a, and the magnetic field detection data 55 of the respective detection coils 25 corresponding to the plurality of generation coils 39.

Since the subsequent processing is the same as that of the above first embodiment, the specific description thereof will be omitted. In addition, since the endoscope system 9 of the second embodiment is basically the same as that of the above first embodiment except for the switching control of the generation coils 39 and the determination processing and the position detection processing in the navigation device 12, basically the same effects as those of the above first embodiment are obtained.

Endoscope System of Third Embodiment

Next, the endoscope system 9 of a third embodiment will be described. In the above first embodiment, the determination of the correspondence relationship 75 based on the frame start signals VD is enabled by synchronously performing the switching control of the generation coils 39 in the magnetic field generator 13, and the detection and the addition of the total magnetic field detection data 55 in the endoscope 10 with the frame start signals VD (reference signals) as references. In contrast, in the third embodiment, the determination of the correspondence relationship 75 between the respective generation coils 39 and the respective magnetic field detection data 55 is enabled by a method different from the first embodiment.

Figure 12:
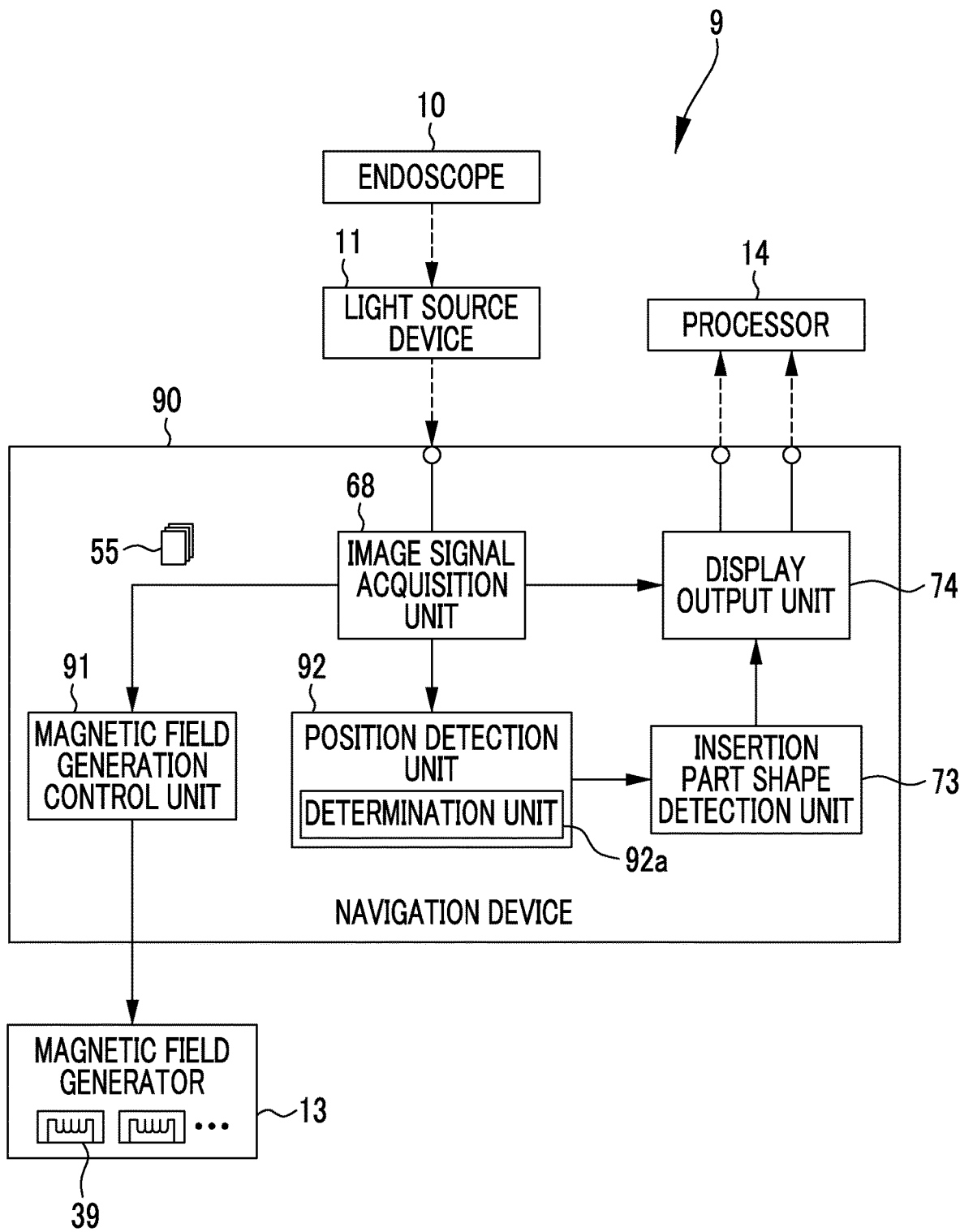
FIG. 12 is a block diagram illustrating a configuration of an endoscope system of a third embodiment.

FIG. 12 is a block diagram illustrating the configuration of the endoscope system 9 of the third embodiment. In addition, since the endoscope system 9 of the third embodiment has basically the same configuration as that of the above first embodiment excluding including a navigation device 90 different from the first embodiment, the same functions and components as those of the above first embodiment will be designated by the same reference signs, and the description thereof will be omitted.

As illustrated in FIG. 12, the navigation device 90 has a magnetic field generation control unit 91 and a position detection unit 92 that are different from those of the first embodiment in addition to the image signal acquisition unit 68, the insertion part shape detection unit 73, and the display output unit 74 of the first embodiment.

Figure 13:
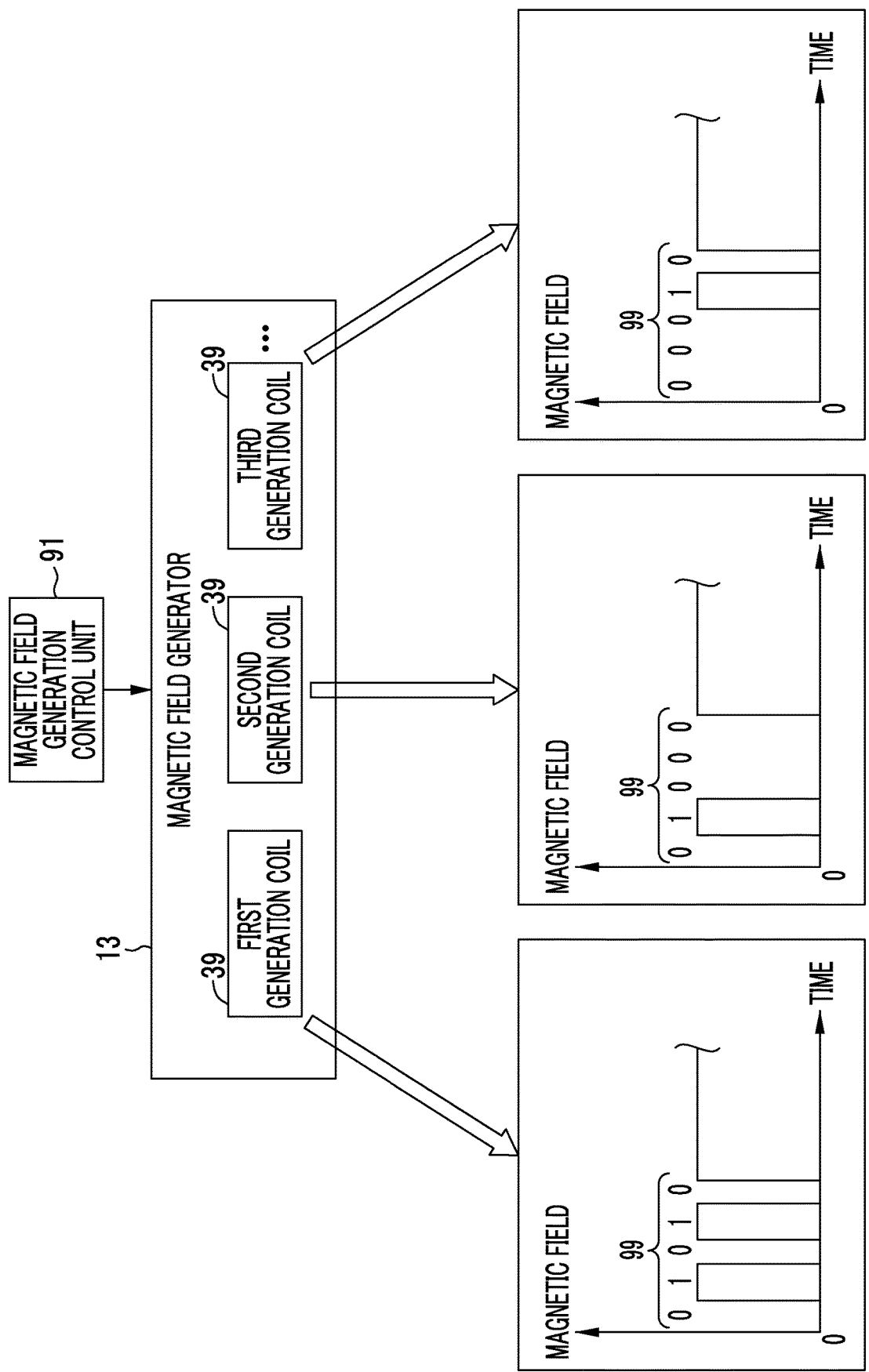
FIG. 13 is an explanatory view for explaining a switching control of respective generation coils by a magnetic field generation control unit of the third embodiment.

FIG. 13 is an explanatory view for explaining the switching control of the respective generation coils 39 by the magnetic field generation control unit 91 of the third embodiment. As illustrated in FIG. 13, the magnetic field generation control unit 91 causes magnetic fields to be generated at different timings from the respective generation coils 39 of the magnetic field generator 13. Additionally, in this case, for example, the magnetic field generation control unit 91 causes magnetic fields to be generated in different generation patterns 99 (indicated by 0 and 1 in the drawing) for the respective generation coils 39 in a first predetermined period. In addition, the "different generation patterns 99" referred to herein indicates that at least one of the waveforms (including amplitudes) and the frequencies of the magnetic fields is different.

Although the switching frequencies of the respective generation coils 39 are not limited, the switching frequencies are set to, for example, frequencies at which the switching of the generation coils 39 establishes at least one cycle, during one cycle of the reference signals (during the frame start signals VD) (refer to FIG. 5).

For example, the magnetic field detection control unit 58 (refer to FIG. 2) of the third embodiment monitors the waveforms of the magnetic field detection data 55 detected by the respective detection coils 25 via the magnetic field detection circuit 49, and acquires the magnetic field detection data 55 from the respective detection coils 25 via the magnetic field detection circuit 49 whenever the waveforms of the magnetic field detection data 55 are switched along with the switching of the generation patterns 99 of the magnetic fields. Accordingly, also in a third embodiment, similarly to the above first embodiment, the total magnetic field detection data 55 acquired by the magnetic field detection control unit 58 is output to the image signal output unit 59, and is added to the signal invalid regions ND between the frame image signals 61. Then, similarly to the above first embodiment, the frame image signals 61 to which the frame start signals VD and the total magnetic field detection data 55 are added are acquired by the image signal acquisition unit 68 of the navigation device 90 via the light source device 11.

Figure 14:
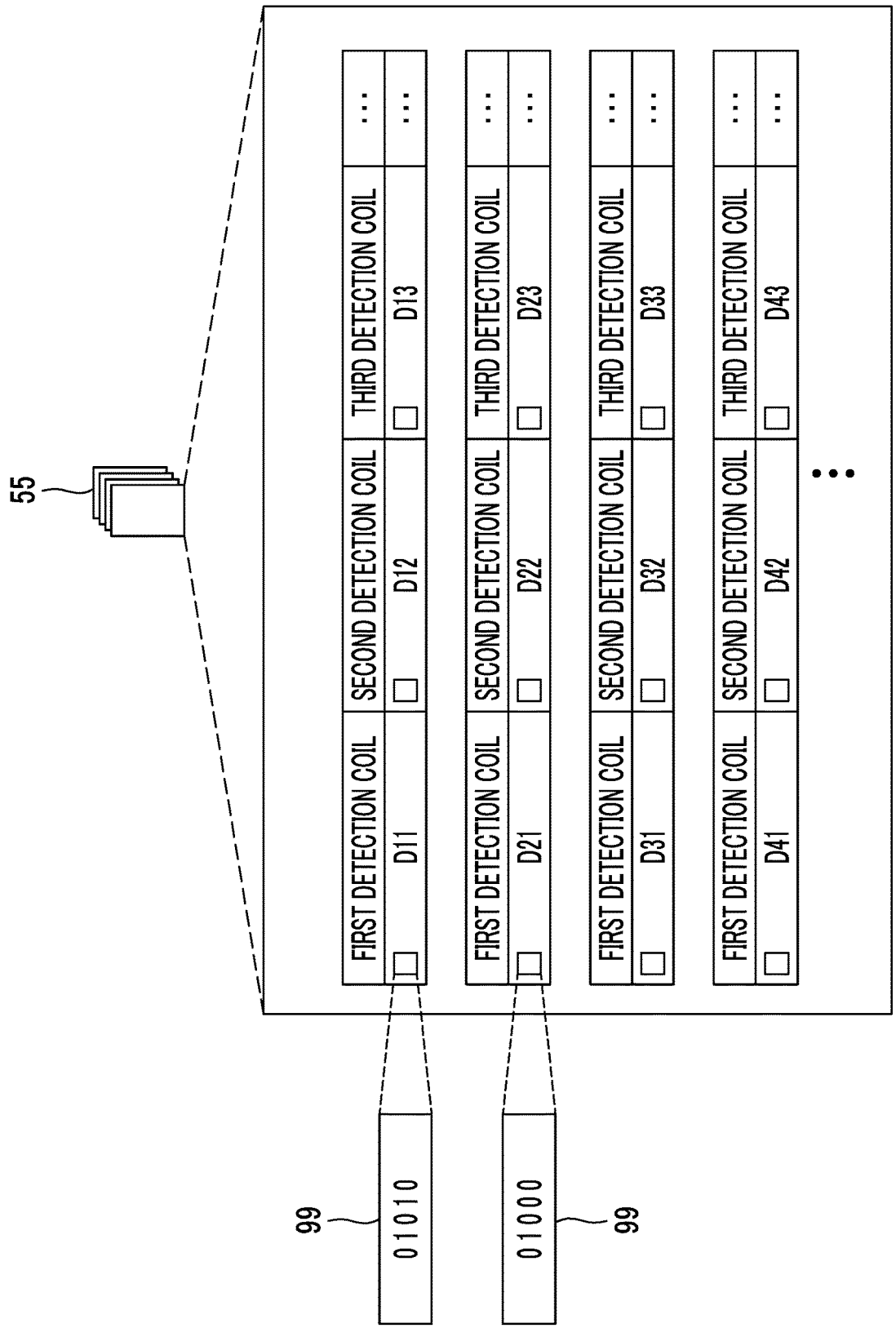
FIG. 14 is an explanatory view for explaining an example of all magnetic field detection data of the third embodiment.

FIG. 14 is an explanatory view for explaining an example of the total magnetic field detection data 55 of the third embodiment. As illustrated in FIG. 14, data showing the generation patterns 99 of the magnetic fields generated by the generation coils 39 is included in the respective items of the total magnetic field detection data 55. For this reason, in the third embodiment, the data of the generation patterns 99 in the respective items of the total magnetic field detection data 55 is the specification information of the invention for specifying the generation coils 39 that are magnetic field generation origins.

Referring back to FIG. 12, the position detection unit 92 of the third embodiment serially detects the total magnetic field detection data 55 for the respective signal invalid regions ND of the frame image signals 61 newly acquired by the image signal acquisition unit 68, and detects the positions of the respective detection coils 25 on the basis of the detected total magnetic field detection data 55.

First, a determination unit 92a provided in the position detection unit 92 analyzes the data of the generation patterns 99 included in the respective items of the total magnetic field detection data 55, thereby performing the determination processing of determining the aforementioned correspondence relationship 75. As earlier described, the data of the generation patterns 99 included in the respective items of the total magnetic field detection data 55 is different for the respective generation coils 39. For this reason, the determination unit 92a can determine the correspondence relationship 75 by analyzing the data of the respective generation patterns 99 of the total magnetic field detection data 55 (performing comparison with the data of the generation patterns 99 for the known respective generation coils 39).

Next, the position detection unit 92 detects the coil position data 76 similarly to the first embodiment on the basis of the correspondence relationship 75 determined by the determination unit 92a and the previously detected total magnetic field detection data 55, and outputs the coil position data 76 to the insertion part shape detection unit 73. Thereafter, similarly to the first embodiment, the shape detection processing by the insertion part shape detection unit 73 and the output processing by the display output unit 74 are performed, and the observation image 41 and the insertion part shape image 42 are displayed on the monitor 15 by the processor 14.

Figure 15:
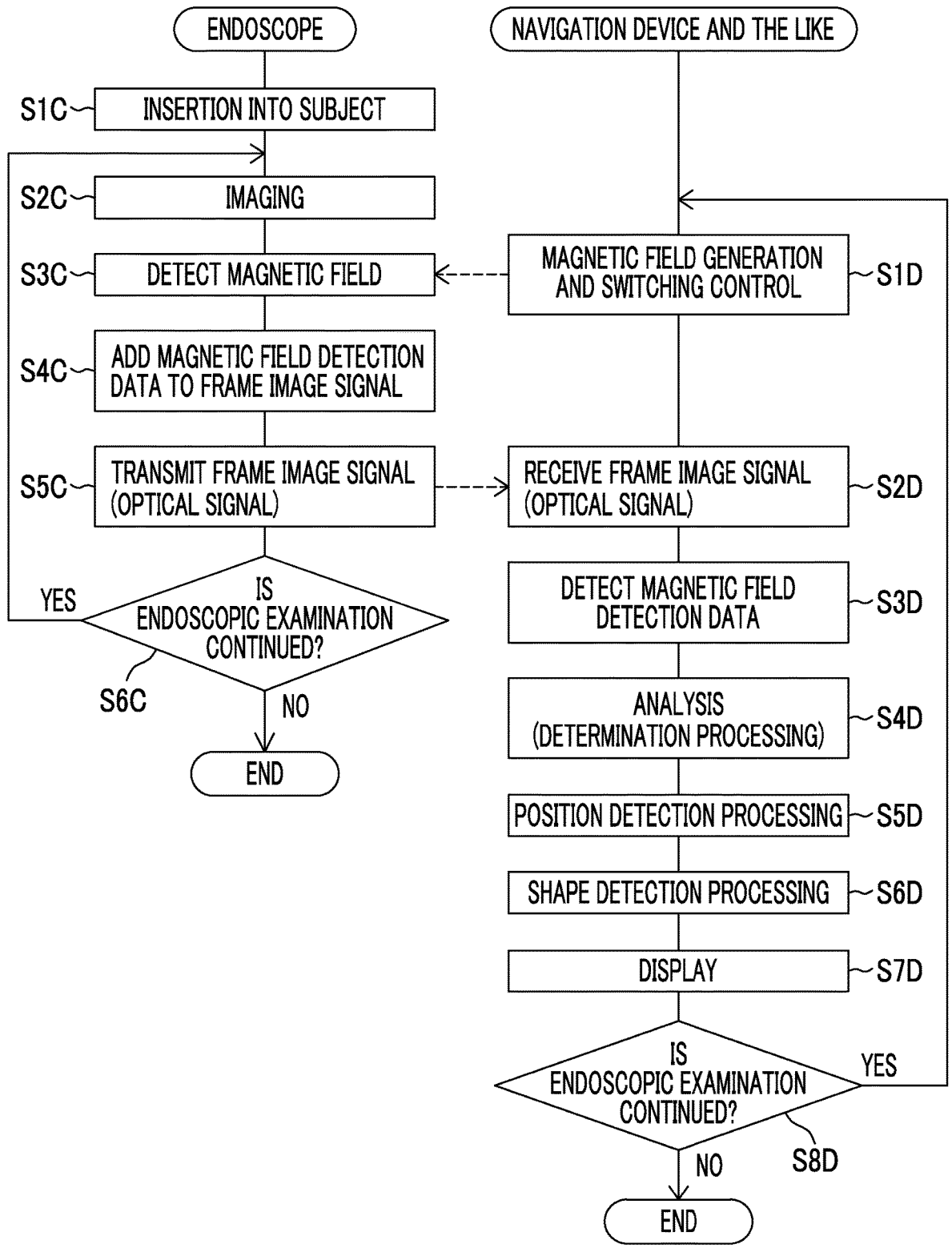
FIG. 15 is a flowchart illustrating a flow of endoscopic examination in the endoscope system of the third embodiment, especially, display processing of an observation image and an insertion part shape image.

Next, the action of the endoscope system 9 of the third embodiment will be described with reference to FIG. 15. In addition, FIG. 15 is a flowchart showing a flow of endoscopic examination in the endoscope system 9 of the third embodiment, especially, display processing (navigation method) of the observation image 41 and the insertion part shape image 42.

In the third embodiment, after the startup of the respective units of the endoscope system 9, similarly to Steps S3A and S4A of the first embodiment, (refer to FIG. 9), the insertion part 17 of the endoscope 10 is inserted into the subject (Step S1C), and imaging of the region to be observed within the subject is started (Step S2C).

Additionally, simultaneously with this, the magnetic field generation control unit 91 of the navigation device 90 performs the switching control of causing the magnetic fields to be generated at different timings and in different generation patterns 99 from the respective generation coils 39 of the magnetic field generator 13 at preset switching frequencies (Step S1D; equivalent to the magnetic field generation control step of the invention). Accordingly, the magnetic fields generated for the respective generation coils 39 in the respective detection coils 25 within the insertion part 17 are detected (Step S3C).

Then, the magnetic field detection control unit 58 of the endoscope 10 acquires the magnetic field detection data 55 obtained by detecting the magnetic fields, which are respectively generated for the respective generation coils 39, with the respective detection coils 25, from the respective detection coils 25 via the magnetic field detection circuit 49. Then, the magnetic field detection control unit 58 outputs the total magnetic field detection data 55 of the respective detection coils 25 for the respective generation coils 39 to the image signal output unit 59. Accordingly, similarly to the first embodiment, the total magnetic field detection data 55 is added to the signal invalid regions ND between the frame image signals 61 (Step S4C).

Next, similarly to the above first embodiment, the frame image signals 61 to which the total magnetic field detection data 55 is added is output to the LD 36 via the signal cable 32, and the optical signals obtained by converting the frame image signals 61 are transmitted toward the PD 37 of the light source device 11 (Step S5C). In addition, as described in the first embodiment, the frame start signals VD are also added to the frame image signals 61.

The optical signals transmitted from the LD 36 are received in the PD 37 of the light source device 11, are converted into the original frame image signals 61 that are electrical signals, and are then output to the image signal acquisition unit 68 of the navigation device 90 via the light source control unit 64 and the communication interfaces 65 (Step S2D; equivalent to the image signal acquisition step of the invention).

Then, the image signal acquisition unit 68, which has acquired the newly output frame image signals 61 from the light source control unit 64, outputs the frame image signals 61 to the display output unit 74.

In this case, the position detection unit 92 detects the total magnetic field detection data 55 from the signal invalid regions ND corresponding to the frame image signals 61 newly acquired by the image signal acquisition unit 68 (Step S3D). Then, the determination unit 92a analyzes the data of the generation patterns 99 included in the respective items of the total magnetic field detection data 55, thereby performing the determination processing of determining the correspondence relationship 75 of the generation coils 39 corresponding to the respective items of the total magnetic field detection data 55 (Step S4D).

Next, the position detection unit 92 performs the position detection processing of detecting the coil position data 76 similarly to the first embodiment on the basis of the correspondence relationship 75 determined by the determination unit 92a and the previously detected total magnetic field detection data 55, and outputs the detected coil position data 76 to the insertion part shape detection unit 73 (Step S5D; equivalent to the position detection step of the invention).

Thereafter, similarly to the first embodiment, the shape detection processing (Step S6D) according to the insertion part shape detection unit 73, the output processing of the frame image signals 61 and the insertion part shape data 78 by the display output unit 74, and the display processing (Step S7D) of the observation image 41 and the insertion part shape image 42 to the monitor 15 by the processor 14 are executed.

Thereafter, the processing from the aforementioned Steps S2C to S5C is repeatedly executed until the endoscopic examination is completed, and the frame image signals 61 to which the total magnetic field detection data 55 is added are serially output from the endoscope 10 to the navigation device 90 (Step S6C). Additionally, in accordance therewith, the processing from the aforementioned Steps S1D to S7D is repeatedly executed in the navigation device 90, the processor 14, and the like, and the switching control of the generation coils 39 and the display of the observation image 41 and the insertion part shape image 42 are consecutively performed (Step S8D).

As described above, in the endoscope system 9 of the third embodiment, by generating the magnetic fields in the different generation patterns 99 for the respective generation coils 39, the generation coils 39 corresponding to the respective items of the total magnetic field detection data 55 can be determined from the data of the generation patterns 99 included in the respective items of the total magnetic field detection data 55 in the navigation device 90. As a result, similarly to the first embodiment, the positions of the respective detection coils 25 can be detected, and the shape and the distal end position PT of the insertion part 17 within the subject can be obtained.

Additionally, the frame image signals 61 to which the total magnetic field detection data 55 is added is output from the endoscope 10 to the navigation device 90. Thus, it is unnecessary to separately provide the endoscope 10 with the output system for outputting the total magnetic field detection data 55 to the navigation device 12. As a result, the same effects as those of the above first embodiment are obtained.

In addition, in the above third embodiment, the switching frequencies of the respective generation coils 39 are set to the frequencies such that the switching of the generation coils 39 establishes one cycle during one cycle of the aforementioned reference signals. However, for example, the switching frequencies of the respective generation coils 39 may be set to the same (including almost the same) frequencies as the aforementioned reference signals, similarly to the above second embodiments. In this case, similarly to the above second embodiment, the coil position data 76 of the respective detection coils 25 is detected on the basis of the magnetic field detection data 55 of the respective detection coils 25 corresponding to the plurality of frame image signals 61.

Others

In the above respective embodiments, a case where the magnetic field detection data 55 is added to the signal invalid regions ND between the frame image signals 61 corresponding to the blank times BT (perpendicular blank times) of the imaging element 53 has been described. However, for example, the magnetic field detection data 55 may be added to headers or the like of the respective frame image signals 61, and a method of adding the magnetic field detection data 55 to the frame image signals 61 is not particularly limited.

In the above respective embodiments, the endoscope system 9, which converts the frame image signals 61 into the optical signals and transmits the converted optical signals from the endoscope 10 to the light source device 11, has been described as an example. However, the invention can also be applied to a case where the endoscope 10 and the light source device 11 are electrically connected to each other, and the frame image signals 61 are transmitted from the endoscope 10 to the light source device 11 as they are in the form of electrical signals. Additionally, the frame image signals 61 may be directly transmitted from the endoscope 10 to the navigation device 12 or 90 without going through the light source device 11.

In the above respective embodiments, one used for the examination of the alimentary canal as the endoscope 10 has been described as an example. However, the type and the application of the endoscope 10 are not particularly limited. Additionally, the invention can be applied to a hard endoscope as well as the flexible endoscope particularly in a case where the distal end position PT of the insertion part 17 is intended to detect (ascertain).

In the above respective embodiments, the magnetic fields are generated from the respective generation coils 39 of the magnetic field generator 13, and the magnetic fields are detected by the respective detection coils 25 within the insertion part 17 of the endoscope 10. However, the magnetic field generation method and the magnetic field detection method are not limited to the method and the configuration that have been described in the above respective embodiments, and the generation and the detection of the magnetic fields may be performed using well-known magnetic field generation units and magnetic field detection units other than the coils.

In the above respective embodiments, the light source device 11, the navigation device 12, and the processor 14 are separately provided. However, at least two of these may be integrated with each other.

In the above respective embodiments, as the specification information of the invention, the data of the frame start signals VD and the generation patterns 99 has been described as an example. However, the specification information is not particularly limited as long as specification information capable of specifying the generation coils 39 that are magnetic field generation origins.

In the above respective embodiments, the endoscope 10 and the navigation device 12 or 90 are provided at the same location. However, the endoscope 10 and the navigation device 12 or 90 may be provided at different locations. In this case, the navigation device 12 or 90 acquires the frame image signals 61 imaged by the endoscope 10 via various communication networks to detect the coil position data 76 of the respective detection coils 25. Additionally, the navigation device 12 or 90 may acquire the frame image signals 61 imaged in the past from a server or the like to detect the coil position data 76 of the respective detection coils 25.

EXPLANATION OF REFERENCES

9: endoscope system
10: endoscope
11: light source device
12: navigation device
13: magnetic field generator
14: processor
15: monitor
17: insertion part
18: operating part
19: universal cord
21: flexible part
22: bending part
23: distal end part
25: detection coil
27: bendable operation knob
28: air/water supply button
29: suction button
31: treatment tool introduction port
32: signal cable
33: light guide
34: connector
36: LD
37: PD
39: generation coil
41: observation image
42: insertion part shape image
45: irradiation lens
46: illumination window
47: observation window
48: imaging device
49: magnetic field detection circuit
49a: preamplifier
49b: A/D conversion circuit
50: overall control circuit
52: condensing lens
53: imaging element
53a: oscillation unit
55: magnetic field detection data
57: signal processing unit
58: magnetic field detection control unit
59: image signal output unit
61: frame image signal
63: illumination light source
64: light source control unit
65: communication interface
68: image signal acquisition unit
69: signal detection unit
70: TG
71: magnetic field generation control unit
72: position detection unit
72a: determination unit
73: insertion part shape detection unit
74: display output unit
75: correspondence relationship
75A: correspondence relationship
76: coil position data
78: insertion part shape data
80A: communication interface
80B: communication interface
82: display input unit
83: display control unit
90: navigation device
91: magnetic field generation control unit
92: position detection unit
92a: determination unit
99: generation pattern
BT: blank time
ND: signal invalid region
PT: distal end position
S1A TO S8A, S1B TO S12B: action of endoscope system
S1C TO S6C, S1D TO SBD: action of endoscope system
VD: frame start signal
XYZ: orthogonal coordinate system

What is claimed is:

1. A navigation device used for an endoscope having an insertion part to be inserted into a subject, an imaging element provided on a distal end side of the insertion part, and a plurality of magnetic field detection coils that are provided within the insertion part and detect magnetic fields, the navigation device comprising:
a processor configured at least to:
control the magnetic fields to be generated at different timings from a plurality of magnetic field generation coils that generate the magnetic fields at mutually different positions;
acquire, from the endoscope, an added image signal obtained by adding specification information for specifying the magnetic field generation coils generating the magnetic fields and magnetic field detection results of the respective magnetic field detection coils to an image signal output from the imaging element as the added image signal comprises a plurality of frame signals and magnetic field detection results; and detect positions of the respective magnetic field detection coils on the basis of the specification information and the magnetic field detection results that are added to the added image signal acquired by the processor, wherein the image signal is a plurality of frame image signals that constitute a dynamic image, and the added image signal is added frame image signals obtained by adding the specification information and the magnetic field detection results to the frame image signals, wherein the specification information includes frame start signals showing start of the added frame image signals, wherein the processor is configured to perform switching of the magnetic field generation coils generating the magnetic fields on the basis of the frame start signals added to the added frame image signals acquired by the processor, and wherein the processor is further configured to perform determination processing of determining a correspondence relationship between the magnetic field detection results added to the added frame image signals and the magnetic field generation coils, on the basis of the frame start signals added to the added frame image signals, and position detection processing of detecting the positions of the respective magnetic field detection coils from the magnetic field detection results, on the basis of the correspondence relationship determined by the determination processing.

2. The navigation device according to claim 1,
wherein the image signal is the plurality of frame image signals that constitute the dynamic image, and the added image signal is added frame image signals obtained by adding the specification information and the magnetic field detection results to the frame image signals, and wherein the magnetic field detection results are added to a signal invalid region between the added frame image signals corresponding to a blank time of the imaging element.

3. The navigation device according to claim 1,
wherein the processor is configured to acquire the added image signal from the endoscope by performing non-contact communication with the endoscope.

4. The navigation device according to claim 1, wherein the processor is further configured to:
detect a shape of the insertion part within the subject on the basis of a position detection result obtained by the processor.

5. The navigation device of claim 1, wherein each of the plurality of frame signals is followed by one of the magnetic field detection results located within a blank time located after each frame signal.

6. A navigation device used for an endoscope having an insertion part to be inserted into a subject, an imaging element provided on a distal end side of the insertion part, and a plurality of magnetic field detection coils that are provided within the insertion part and detect magnetic fields, the navigation device comprising:
a processor configured at least to:
control the magnetic fields to be generated at different timings from a plurality of magnetic field generation coils that generate the magnetic fields at mutually different positions;
acquire, from the endoscope, an added image signal obtained by adding specification information for specifying the magnetic field generation coils generating the magnetic fields and magnetic field detection results of the respective magnetic field detection coils to an image signal output from the imaging element as the added image signal comprises a plurality of frame signals and magnetic field detection results; and detect positions of the respective magnetic field detection coils on the basis of the specification information and the magnetic field detection results that are added to the added image signal acquired by the processor, wherein the image signal is a plurality of frame image signals that constitute a dynamic image, and the added image signal is added frame image signals obtained by adding the specification information and the magnetic field detection results to the frame image signals, wherein the processor is configured to control the magnetic fields to be generated in different generation patterns for the respective magnetic field generation coils, wherein the specification information determines a structure of the generation patterns in the magnetic field detection results, and wherein the processor is configured to perform determination processing of determining the magnetic field generation coils corresponding to the magnetic field detection results on the basis of the generation patterns detected from the magnetic field detection results added to the added image signal, and position detection processing of detecting the positions of the respective magnetic field detection coils from the magnetic field detection results, on the basis of the determination results of the determination processing.

7. The navigation device according to claim 6,
wherein the image signal is the plurality of frame image signals that constitute the dynamic image, and the added image signal is added frame image signals obtained by adding the specification information and the magnetic field detection results to the frame image signals, and wherein the magnetic field detection results are added to a signal invalid region between the added frame image signals corresponding to a blank time of the imaging element.

8. The navigation device according to claim 6,
wherein the processor is configured to acquire the added image signal from the endoscope by performing non-contact communication with the endoscope.

9. The navigation device according to claim 6, further configured to:
detect a shape of the insertion part within the subject on the basis of a position detection result obtained by the processor.

10. An endoscope system comprising:
an endoscope having an insertion part to be inserted into a subject, an imaging element provided on a distal end side of the insertion part, and a plurality of magnetic field detection coils that are provided within the insertion part and detect magnetic fields;
a plurality of magnetic field generation coils that generate the magnetic fields; and
the navigation device according to claim 1.

11. The endoscope system according to claim 10,
wherein a processor of the endoscope is further configured to add the specification information for specifying the magnetic field generation coils generating the magnetic fields and the magnetic field detection results for the respective magnetic field detection coils, to the image signal output from the imaging element, and outputs the added image signal, to which the specification information and the magnetic field detection results are added, to the navigation device.

12. The endoscope system according to claim 10, wherein the magnetic field generation coils are provided at positions different from the endoscope.

13. An endoscope system comprising:
an endoscope having an insertion part to be inserted into a subject, an imaging element provided on a distal end side of the insertion part, and a plurality of magnetic field detection coils that are provided within the insertion part and detect magnetic fields;
a plurality of magnetic field generation coils that generate the magnetic fields; and
the navigation device according to claim 6.

14. The endoscope system according to claim 13, wherein a processor of the endoscope is further configured to add the specification information for specifying the magnetic field generation coils generating the magnetic fields and the magnetic field detection results for the respective magnetic field detection coils, to the image signal output from the imaging element, and outputs the added image signal, to which the specification information and the magnetic field detection results are added, to the navigation device.

15. The endoscope system according to claim 13, wherein the magnetic field generation coils are provided at positions different from the endoscope.

16. A navigation method used for an endoscope having an insertion part to be inserted into a subject, an imaging element provided on a distal end side of the insertion part, and a plurality of magnetic field detection coils that are provided within the insertion part and detect magnetic fields, the navigation method comprising:
a magnetic field generation control step of causing the magnetic fields to be generated at different timings from a plurality of magnetic field generation coils that generate the magnetic fields at mutually different positions;
an image signal acquisition step of acquiring, from the endoscope, an added image signal obtained by adding specification information for specifying the magnetic field generation coils generating the magnetic fields and magnetic field detection results of the respective magnetic field detection coils to an image signal output from the imaging element as the added image signal comprises a plurality of frame signals and magnetic field detection results; and
a position detection step of detecting positions of the respective magnetic field detection coils on the basis of the specification information and the magnetic field detection results that are added to the added image signal acquired in the image signal acquisition step,
wherein the image signal is a plurality of frame image signals that constitute a dynamic image, and the added image signal is added frame image signals obtained by adding the specification information and the magnetic field detection results to the frame image signals,
wherein the specification information includes frame start signals showing start of the added frame image signals,
wherein the magnetic field generation control step includes switching of the magnetic field generation coils generating the magnetic fields on the basis of the frame start signals added to the added frame image signals acquired by the image signal acquisition step, and
wherein the position detection step includes
determination processing of determining a correspondence relationship between the magnetic field detection results added to the added frame image signals and the magnetic field generation coils, on the basis of the frame start signals added to the added frame image signals, and
position detection processing of detecting the positions of the respective magnetic field detection coils from the magnetic field detection results, on the basis of the correspondence relationship determined by the determination processing.

17. The navigation method according to claim 16, wherein the image signal is the plurality of frame image signals that constitute the dynamic image, and the added image signal is added frame image signals obtained by adding the specification information and the magnetic field detection results to the frame image signals, and
wherein the magnetic field detection results are added to a signal invalid region between the added frame image signals corresponding to a blank time of the imaging element.

18. The navigation method according to claim 16, wherein the image signal acquisition step includes acquiring the added image signal from the endoscope by performing noncontact communication with the endoscope.

19. The navigation method according to claim 16, further comprising
an insertion part shape detection step of detecting a shape of the insertion part within the subject on the basis of a position detection result obtained by the position detection step.

20. A navigation method used for an endoscope having an insertion part to be inserted into a subject, an imaging element provided on a distal end side of the insertion part, and a plurality of magnetic field detection coils that are provided within the insertion part and detect magnetic fields, the navigation method comprising:
a magnetic field generation control step of causing the magnetic fields to be generated at different timings from a plurality of magnetic field generation coils that generate the magnetic fields at mutually different positions;
an image signal acquisition step of acquiring, from the endoscope, an added image signal obtained by adding specification information for specifying the magnetic field generation coils generating the magnetic fields and magnetic field detection results of the respective magnetic field detection units to an image signal output from the imaging element as the added image signal comprises a plurality of frame signals and magnetic field detection results; and
a position detection step of detecting positions of the respective magnetic field detection coils on the basis of the specification information and the magnetic field detection results that are added to the added image signal acquired in the image signal acquisition step,
wherein the magnetic field generation control step causes the magnetic fields to be generated in different generation patterns for the respective magnetic field generation units,
wherein the specification information determines a structure of the generation patterns in the magnetic field detection results, and
wherein the position detection step includes determination processing of determining the magnetic field generation coils corresponding to the magnetic field detection results on the basis of the generation patterns detected from the magnetic field detection results added to the added image signal, and position detection processing of detecting the positions of the respective magnetic field detection coils from the magnetic field detection results, on the basis of the determination results of the determination processing.

21. The navigation method according to claim 20, wherein the image signal is the plurality of frame image signals that constitute the dynamic image, and the added image signal is added frame image signals obtained by adding the specification information and the magnetic field detection results to the frame image signals, and wherein the magnetic field detection results are added to a signal invalid region between the added frame image signals corresponding to a blank time of the imaging element.

22. The navigation method according to claim 20, wherein the image signal acquisition step includes acquiring the added image signal from the endoscope by performing noncontact communication with the endoscope.

23. The navigation method according to claim 13, further comprising an insertion part shape detection step of detecting a shape of the insertion part within the subject on the basis of a position detection result obtained by the position detection step.

* * * * *